(12) United States Patent
Smith et al.

(10) Patent No.: US 9,651,487 B2
(45) Date of Patent: May 16, 2017

(54) SURFACE PLASMON RESONANCE COMPATIBLE CARBON THIN FILMS

(75) Inventors: Lloyd M. Smith, Madison, WI (US); Matthew R. Lockett, Madison, WI (US); Michael R. Shortreed, Portage, WI (US); Robert M. Corn, Corona del Mar, CA (US); Stephen Weibel, Madison, WI (US); Robert J. Hamers, Madison, WI (US); Bin Sun, Falls Church, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2675 days.

(21) Appl. No.: 12/037,332

(22) Filed: Feb. 26, 2008

(65) Prior Publication Data
US 2009/0141376 A1  Jun. 4, 2009

Related U.S. Application Data

(60) Provisional application No. 60/903,452, filed on Feb. 26, 2007, provisional application No. 60/962,529, filed on Jul. 30, 2007.

(51) Int. Cl.
 G02B 5/04 (2006.01)
 G01N 21/552 (2014.01)
(52) U.S. Cl.
 CPC .............. *G01N 21/553* (2013.01); *G02B 5/04* (2013.01)
(58) Field of Classification Search
 CPC .............................. G01N 21/553; G02B 5/04
 USPC ........ 359/883, 831, 900; 356/128, 517, 300, 356/445
 See application file for complete search history.

(56) References Cited

U.S. PATENT DOCUMENTS

| | | | |
|---|---|---|---|
| 5,351,127 A | 9/1994 | King et al. | |
| 5,629,213 A | 5/1997 | Kornguth et al. | |
| 5,939,201 A * | 8/1999 | Boire et al. | 428/432 |
| 6,127,129 A | 10/2000 | Corn et al. | |
| 6,330,062 B1 | 12/2001 | Corn et al. | |
| 6,518,572 B1 * | 2/2003 | Kishii et al. | 250/339.08 |
| 6,569,979 B1 | 5/2003 | Strother et al. | |
| 6,713,178 B2 * | 3/2004 | Veerasamy | 428/408 |

(Continued)

OTHER PUBLICATIONS

Blackwell, "Hitting the SPOT: Small-Molecule Macroarrays Advance Combinatorial Synthesis," *Current Opinion Chem. Biol.*, 10:203-212 (2006).

(Continued)

*Primary Examiner* — Ricky D Shafer
(74) *Attorney, Agent, or Firm* — Daniel A. Blasiole; Joseph T. Leone; DeWitt, Ross & Stevens, S.C.

(57) ABSTRACT

SPR-compatible substrates for high density microarray fabrication and analyses are provided. Novel carbon-on-metal thin film substrate architecture permits the integration of surface plasmon resonance detection with photolithographically fabricated biomolecule arrays for the analysis of biomolecular interactions. The utility of the technology is shown in the analysis of specific DNA-DNA, DNA-RNA and DNA-protein binding interactions. These new substrates may be used to determine the secondary structure of RNA molecules, to probe the sequence-specific binding kinetics and affinity of proteins and small molecules, and as substrates for small-molecule combinatorial chemistry platforms for drug discovery applications.

44 Claims, 19 Drawing Sheets

(56) References Cited

U.S. PATENT DOCUMENTS

| | | | |
|---|---|---|---|
| 6,783,253 B2* | 8/2004 | Thomsen et al. | 359/870 |
| 6,798,521 B2 | 9/2004 | Elkind et al. | |
| 6,815,067 B2* | 11/2004 | Ata et al. | 428/408 |
| 6,849,397 B2 | 2/2005 | Nelson et al. | |
| 6,933,112 B1* | 8/2005 | Drewes et al. | 435/6.11 |
| 6,977,722 B2* | 12/2005 | Wohlstadter et al. | 356/246 |
| 7,002,004 B2* | 2/2006 | Corn et al. | 536/24.3 |
| 7,067,322 B2 | 6/2006 | Corn et al. | |
| 7,271,914 B2 | 9/2007 | Lin et al. | |
| 7,276,283 B2* | 10/2007 | Denes et al. | 428/403 |
| 7,420,653 B2* | 9/2008 | Kurt | 355/67 |
| 7,989,220 B2* | 8/2011 | Lakowicz et al. | 436/525 |
| 2002/0193030 A1* | 12/2002 | Yao et al. | 442/366 |
| 2003/0017579 A1* | 1/2003 | Corn et al. | 435/287.2 |
| 2006/0014155 A1* | 1/2006 | Hamers et al. | 435/6 |
| 2006/0154304 A1* | 7/2006 | Han et al. | 435/7.1 |
| 2008/0044451 A1* | 2/2008 | Steinmuller-Nethl et al. | 424/423 |
| 2009/0192297 A1* | 7/2009 | Yoshida et al. | 530/402 |

OTHER PUBLICATIONS

Frutos et al., "Near-infrared Surface Plasmon Resonance Measurements of Ultrathin Films. 2. Fourier Transform SPR Spectroscopy," *Anal. Chem.*, 71:3935-3940 (1999).
Gillmor et al., "Hydrophilic/Hydrophobic Patterned Surfaces as Templates for DNA Arrays," *Langmuir*. 16:7223-7228 (2000).
Guo et al., "Direct Fluorescence Analysis of Genetic Polymorphisms by Hybridization with Oligonucleotide Arrays on Glass Supports," *Nucleic Acids Research*, 22(24):5456-5465 (1994).
Homola et al., "Surface Plasmon Resonance Sensors: Review," *Sensors and Actuators B Chemical*, 54:3-15 (1999).
Knickerbocker et al., "DNA-Modified Diamond Surfaces," *Langmuir*, 19:1938-1942 (2003).
Kretschmann and Raether, "Radiative Decay of Non Radiative Surface Plasmons Excited by Light," *Zeitschrift Fur Naturforschrung Part A—Astrophysik, Physik, und Physikalische Chemie*, 23(a): 2135-2136 (1968).
Mitsushio et al., "Sensor properties and surface characterization of the metal-deposited SPR optical fiber sensors with Au, Ag, Cu, and A1," *Sensors and Actuators A*, 125:296-303 (2006).
Nedelkov, "Development of Surface Plasmon Resonance Mass Spectrometry Array Platform," *Anal. Chem.*, 79:5987-5990 (2007).
Nelson et al., "Surface Plasmon Resonance Biomolecular Interaction Analysis Mass Spectrometry. 1. Chip-Based Analysis," *Anal. Chem.*, 69: 4363-4368 (1997).
Norris et al., "Mass Spectrometry of Intracellular and Membrane Proteins Using Cleavable Detergents," *Anal. Chem.*, 75:6642-6647 (2003).
Ordal et al., "Optical properties of the Metals A1, Co, Cu Au, Fe Pb, Ni, Pd, Pt, Ag, Ti and W in the Infrared and Far Infrared," *Applied Optics*, 22:1099-1120 (1983).
Otto, "Excitation of Nonradiative Surface Plasma Waves in Silver by the Method of Frustrated Total Reflection," *Zeitschrift Für Physik*, 216:398-410 (1968).
Peelen and Smith, "Immobilization of Amine-Modified Oligonucleotides on Aldehyde-Terminated Alkanethiol Monolayers on Gold," *Langmuir*, 21:266-271 (2005).
Phillips et al., "In site Oligonucleotide Synthesis on Carbon Materials: Stable Substrates for Microarray Fabrication," *Nucl. Acids. Res.*, 36(1):e7, 9 pages (2008).
Rogers et al., "Immobilization of Oligonucleotides onto a Glass Support via Disulfide Bonds: A Method for Preparation of DNA Microarrays," *Anal. Biochem.*, 266:23-30 (1999).
Shumaker-Parry and Campbell, "Quantitative Methods for Spatially Resolved Adsorption/Desorption Measurements in Real Time by Surface Plasmon Resonance Microscopy," *Anal. Chem.*, 76:907-917 (2004).
Singh-Gasson et al., "Maskless Fabrication of Light-Directed Oligonucleotide Microarrays Using a Digital Micromirror Array," *Nature Biotechnology*, 17: 974-978 (1999).
Stenberg et al., "Quantitative Determination of Surface Concentration of Protein with Surface Plasmon Resonance Using Radiolabeled Proteins," *J. Colloid and Interface Science*, 143(2):513-526 (1991).
Strother et al., "Photochemical Functionalization of Diamond Films" *Langmuir*, 18:968-971 (2002).
Sun et al., "Covalent Photochemical Functionalization of Amorphous Carbon This Films for Integrated Real-Time Biosensing," *Langmuir*, 22:9598-9605 (2006).
Thiede et al., "Peptide Mass Fingerprinting," *Methods*, 35:237-247 (2005).
Thomas et al, "Desorption/Ionization of Silicon (DIOS): A Diverse Mass Spectrometry Platform for Protein Characterization," *Proc. Natl. Acad. Sci. USA*, 98(9):4932-9437 (2002).
Thoms and Butler, "HREELS and LEED of H/C(100): the 2x1 Monohydride Dimer Row Reconstruction," *Surface Science*, 328:291-301 (1995).
Thoms et al., "Production and Characterization of Smooth, Hydrogen-Terminated Diamond C(100)," *Applied Physics Letters*, 65:2957-2959 (1994).
Wang et al., "Multiple Word DNA Computing on Surfaces," *J. Am. Chem. Soc.*, 122(31):7435-7440 (2000).
Wegner et al., "Surface Plasmon Resonance Imaging Measurements of DNA, RNA and Protein Interactions to Biomolecular Arrays," *Protein Microarry Technology*, Wiley-VCH: 2004; p. 107-129.
Yang et al., "DNA-Modified Nanocrystalline Diamond Thin-Films as Stable, Biologically Active Substrates," *Nat. Materials*, 1:253-257 (2002).
Kaminska et al., "Preparation of real time SPR-biosensors for study of protein deposition at titanium and NCD surfaces," Engineering of Biomaterials, vol. I, No. 43044, 2005, pp. 16-20.
Walkowiak, "Surface-Modified Metallic Biomaterials in Contact with Blood and Endothelial Cells," Macromol, SYMP, No. 253, 2007, pp. 122-127.

\* cited by examiner

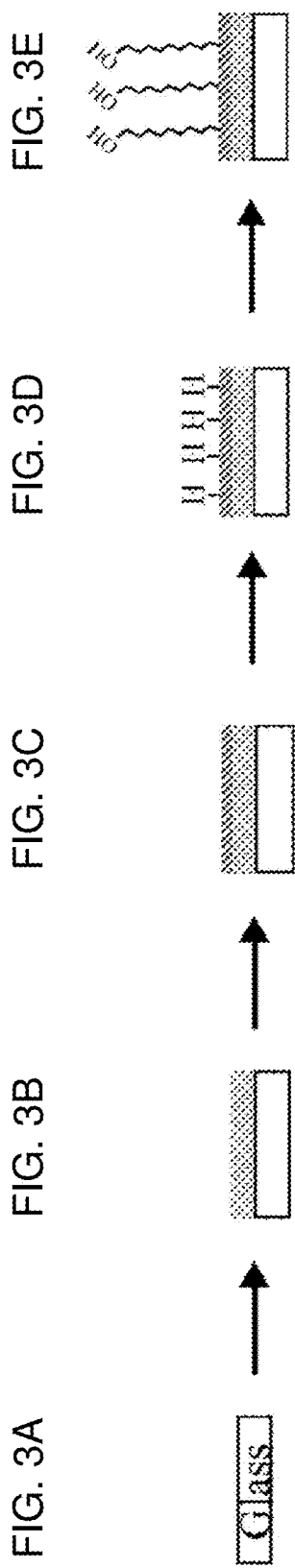

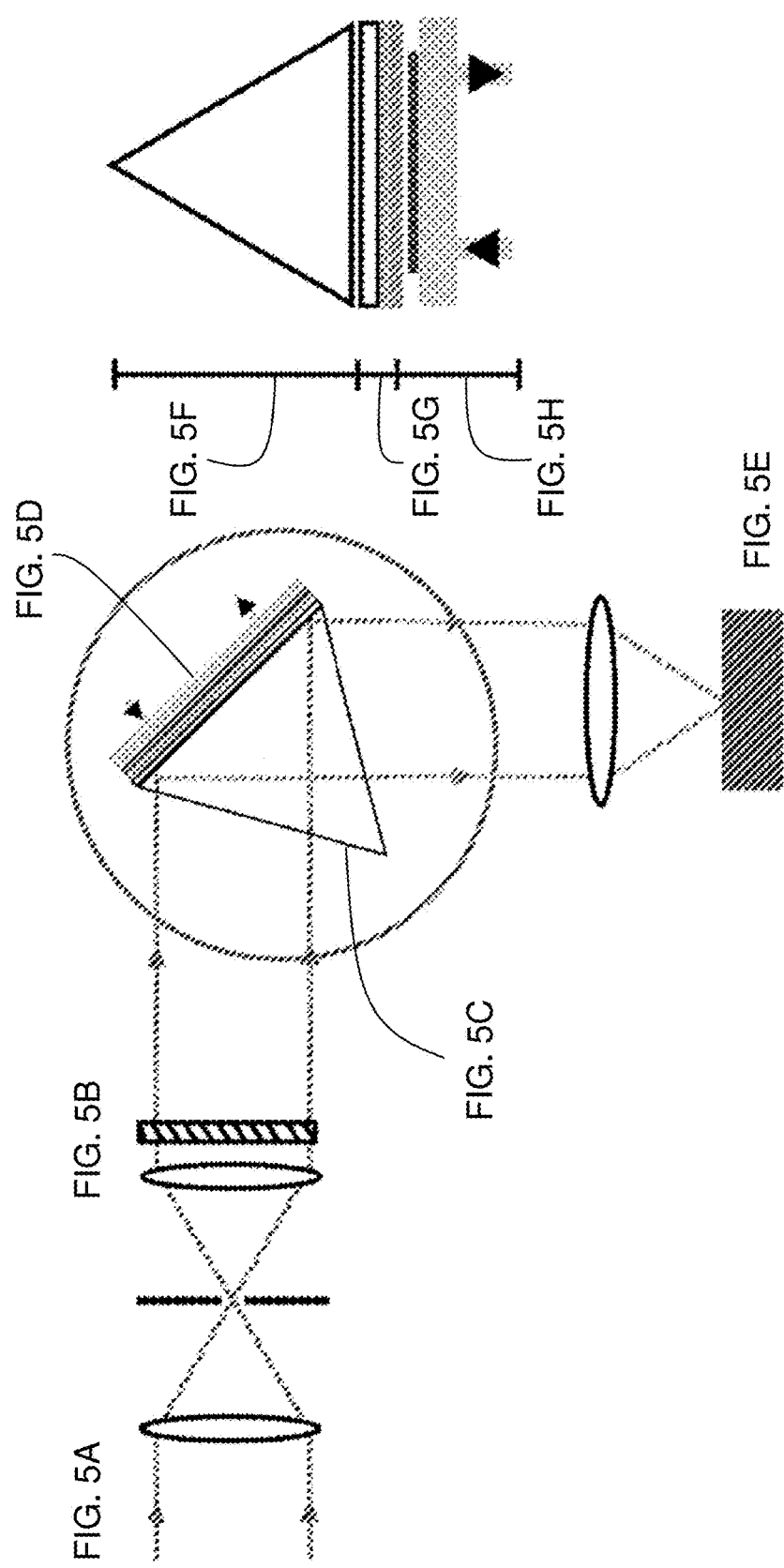

FIG. 6A    FIG. 6B                    FIG. 6C
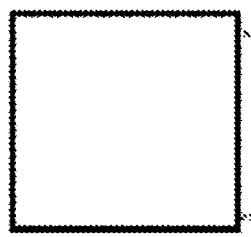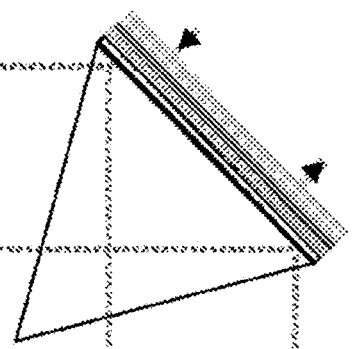

(a) Scanning angle SPR measurements (b) SPR imaging measurements

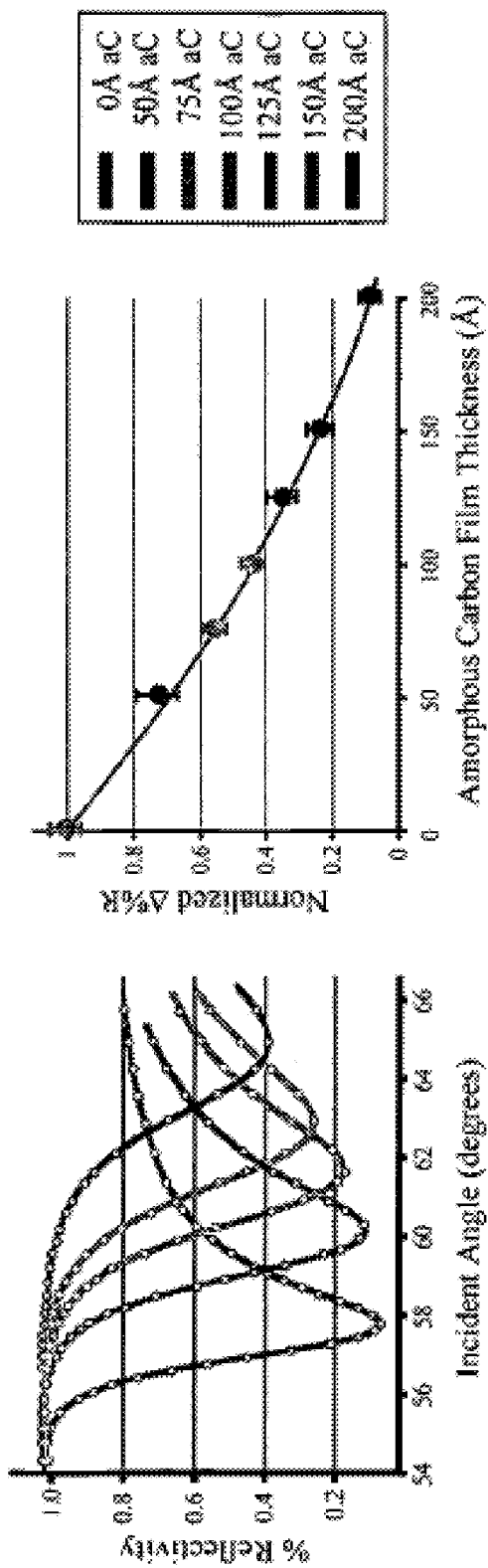

FIG. 10A
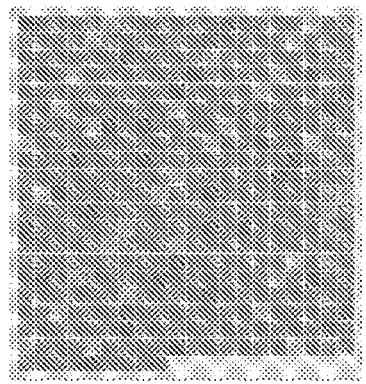
FIG. 10B
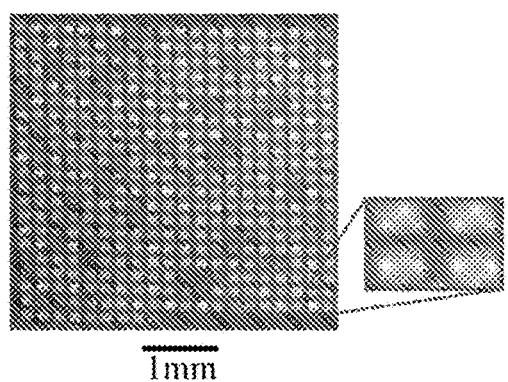
1mm
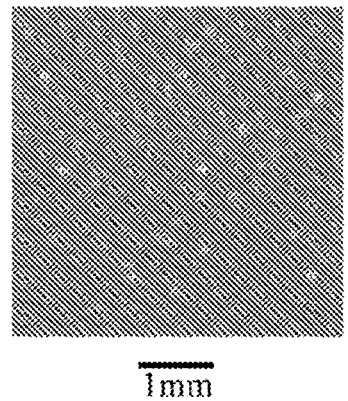
1mm
FIG. 10C
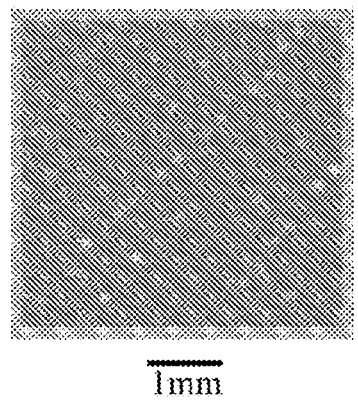
1mm
FIG. 10D

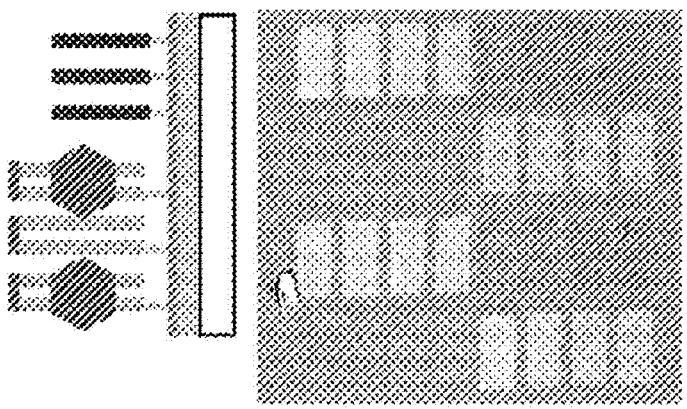
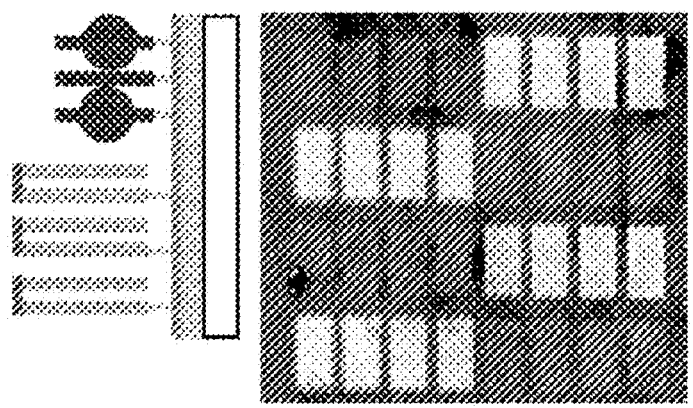
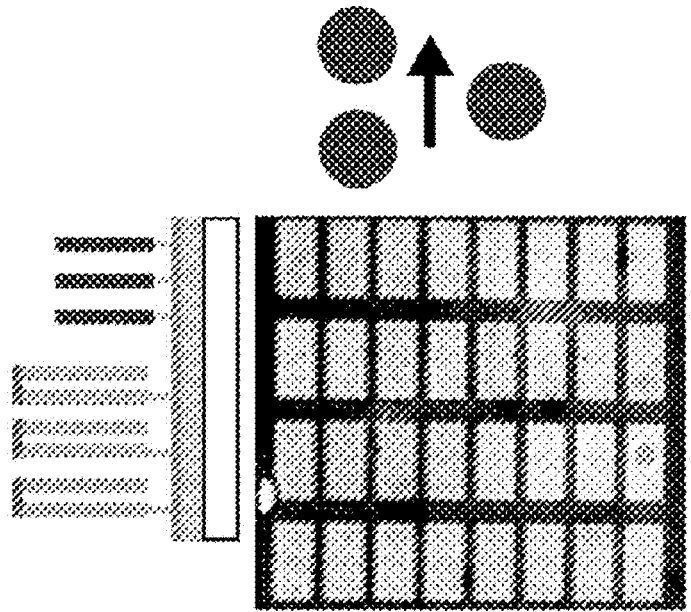

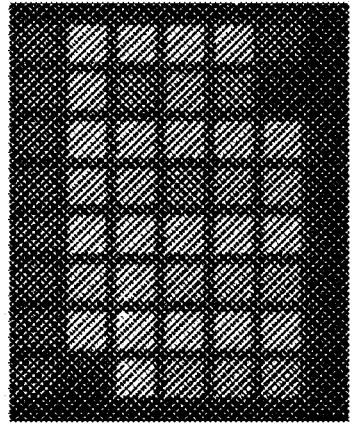
FIG. 12C (c) Array on Amorphous Carbon
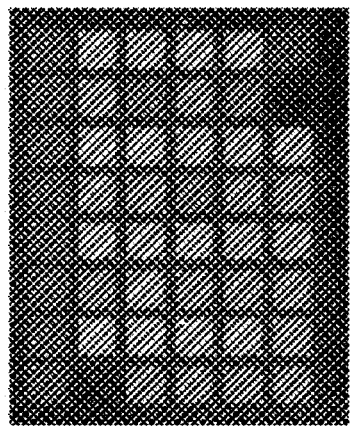
FIG. 12B (b) Array on Glass
FIG. 12A (a) Pattern

SURFACE PLASMON RESONANCE COMPATIBLE CARBON THIN FILMS

CROSS-REFERENCE TO RELATED APPLICATIONS

This invention claims priority to U.S. Provisional Patent Application Ser. Nos. 60/903,452, filed Feb. 26, 2007, and 60/962,529, filed Jul. 30, 2007, both of which are herein incorporated by reference.

GOVERNMENT INTERESTS

This invention was made with government support under HG002298 and DK070297 awarded by the National Institutes of Health and 0203892 awarded by the National Science Foundation. The government has certain rights in the invention.

FIELD OF THE INVENTION

The present invention relates to the field of compositions and methods for functionalization of surfaces in order to bind various molecules.

BACKGROUND

The phenomenon of Surface Plasmon Resonance (SPR), first reported in 1968 (Otto, 1968, *Zeitschrift Fur Physik* 216: 398; Kretschmann and Raether, 1968, Zeitschrift Fur Naturforschrung Part A—Astrophysik, Physik, und Physikalische Chemie A 23: 2135), occurs due to the formation of surface plasmon polaritons, also known as surface plasmons, which are surface electromagnetic waves that propagate parallel to a metal thin film/dielectric interface and as such are very sensitive to changes at the interface (e.g. molecular adsorption). The angle of minimum reflectivity, known as the surface plasmon angle, depends strongly on the refractive index of the medium in contact with the metal surface, with an interaction depth that decays exponentially from the surface. This property has been exploited to form the basis of a highly sensitive and versatile sensing technology for measurements of surface binding in aqueous solutions. In an SPR experiment, a metal thin film is modified with molecules, such as DNA, capable of forming affinity interactions. Upon exposure of the surface to affinity partners, binding occurs that produces a change in reflectivity of the surface. A simple measurement of the amount of reflected light thus provides a sensitive and quantitative measure of surface binding.

An important advantage of SPR is that unlike fluorescence detection, no label is needed, eliminating the need for a labeling step on a molecule that may be easily damaged, and/or present only at a low concentration or purity. Surface plasmon resonance (SPR) imaging has demonstrated its ability to monitor interactions between biological moieties in real-time, without the aid of chemical labels such as fluorophores and radioisotopes. Currently gold surfaces modified with alkane thiol monolayers are used to monitor interactions via SPR. The technique of SPR imaging has proven its utility in monitoring DNA-DNA, DNA-protein, peptide-protein, small molecule-protein, protein-protein interactions; giving a wealth of information pertaining to enzyme kinetics, drug affinity studies, and DNA hybridization studies.

Although SPR is a powerful and widely used platform for the characterization of molecular interactions, like all technologies, it has limitations. For example, while SPR does detect binding, it does not provide much information on the nature of the binding molecule. This has tended to limit the application of the technology to the analysis of already known and purified molecules interacting with one another, and not allowed the technology to be of much use in the analysis of complex mixtures or for the discovery of previously unknown binding partners. In addition, the detection sensitivity is lower than that of some other methods, most notably evanescent wave fluorescence detection. SPR detection is similar to absorption spectrophotometry in that it measures small changes in a large signal (the reflected light). This limits its sensitivity compared to fluorescence in which small amounts of emitted light can be detected in the presence of little background signal, although achieving this in practice can be compromised by fluorescent contaminants and light scattering. Finally, the gold thin film generally employed for SPR measurements is physically fragile and the thiol-gold bonds used to place attachment chemistry on the gold surfaces are not stable to either UV irradiation (often employed in photochemical processes), or to a wide variety of moderate to harsh chemical conditions (e.g. acids, bases, oxidizers, reductants, etc.), limiting the sorts of chemistry that one can utilize on these substrates and compromising its utility for many applications. In addition, the gold surfaces typically employed in SPR experiments cannot be used in the creation of high-density microarrays in systems developed by Nimblegen and Affymetrix, which use UV-light photolithographic methods. Upon exposure to UV light gold-thiol bonds are cleaved, leaving the surface unusable for array fabrication. Thus the fabrication of a substrate that is both SPR-active and chemically robust is necessary to create a usable surface for label-free detection means in highly-parallel and multiplexed experiments, such as those increasingly used and relied upon in the areas of genomics, proteomics, and drug discovery. The present invention addresses these and related needs.

BRIEF SUMMARY

The instant invention provides substrates, which include: a support surface capable of transmitting light; a metallic layer adhered to the support surface; and a carbonaceous layer deposited on the metallic layer. The substrates may also include a plurality of biomolecules attached to the carbonaceous layer.

The instant invention provides substrates, which include: a support surface capable of transmitting light in surface plasmon resonance analysis; a metallic layer adhered to the support surface; and a carbonaceous layer deposited on the metallic layer. The substrates may also include a plurality of biomolecules attached to the carbonaceous layer. The support surface may include a glass block. The support surface may include a layer of SF 10 glass. The carbonaceous layer may include amorphous carbon. The substrates may also include a transparent prism adhered to the support surface. The substrates may include index matching fluid positioned between the transparent prism and the support surface. The biomolecules may be attached to the carbonaceous layer at a density of between about $10^{10}/cm^2$ and about $5 \times 10^{14}/cm^2$. The support surface may be selected from the group consisting of plastic, glass, quartz, fused quartz, and fused silica. The support surface may have a thickness of between about 1 µm and about 10 cm. The metallic layer may be selected from the group consisting of gold, silver, copper, chromium, and aluminum. The metallic layer may have a thickness of between about 1 nm and about 1 µm. The carbonaceous layer may include material selected from the group consisting of amorphous carbon, hydrogenated amorphous carbon, tetrahedral amorphous carbon, and diamond thin film. The carbonaceous material may have a thickness of between about 1 nm and about 1 μm. The biomolecules may be configured in one or more arrays. The biomolecules may be selected from the group consisting of single and double-stranded oligonucleotides, DNA, RNA, proteins, protein fragments, amino acids, peptides, aptamers, antibodies, antigens, lectins, carbohydrates, transcription factors, cellular components, cellular surface molecules, viruses, virus fragments, lipids, hormones, vitamins, and small molecules. The biomolecules may be identical to each other. Alternatively, at least two biomolecules may be different from each other.

The instant invention provides methods for detecting surface plasmon resonance associated with test samples. The methods include: providing a substrate comprising a support surface capable of transmitting surface plasmon resonance analysis light, a metallic layer adhered to the support surface, a carbonaceous layer adhered to the metallic layer, and a plurality of biomolecules attached to the carbonaceous layer; contacting the test sample with the plurality of biomolecules attached to the carbonaceous layer; and detecting surface plasmon resonance associated with the test sample. In the practice of the methods, the biomolecules may be configured in one or more arrays. The methods may also include using mass spectrometric means to analyze molecules from the test sample that are attached to the plurality of biomolecules.

The instant invention provides assays, which include: providing a substrate comprising a support surface capable of transmitting light, metallic layer adhered to the support surface, a carbonaceous layer adhered to the metallic layer, a plurality of biomolecules attached to the carbonaceous layer; contacting the test sample with the plurality of biomolecules attached to the carbonaceous layer; and analyzing molecules from the test sample attached to the plurality of biomolecules using mass spectrometric means.

The instant invention provides methods of making substrates for use in surface plasmon resonance measurements. The methods include: attaching a metallic layer that can support surface plasmons to a transparent material; depositing carbonaceous material onto the metallic layer, to create a carbon thin film; and attaching biomolecules to the carbon thin film. The practice of the methods may include thermally evaporating the metallic layer onto the transparent material. The practice of the methods may include depositing carbonaceous material onto the metallic layer using DC sputtering. In the practice of the methods, the biomolecules may be covalently attached to the carbon thin film using an ultraviolet light-mediated reaction. In the practice of the methods, the biomolecules may be configured in one or more arrays.

The instant invention provides methods for functionalizing a surface to bind biomolecules. The methods include: attaching a metallic film that can support surface plasmons to a transparent support surface; depositing carbonaceous material onto the metallic film, to create a carbon thin film; and covalently attaching biomolecules to the carbon thin film. In the practice of the methods, the transparent support surface may be a dielectric material with a high index of refraction. The transparent support surface may be SF 10 glass. The transparent support surface may be SPR-active support surface. The practice of the methods may include depositing carbonaceous material onto the metallic film using DC sputtering. In the practice of the methods, the biomolecules may be covalently attached to the carbon thin film using an ultraviolet light-mediated reaction. The biomolecules may be configured in one or more arrays.

The instant invention provides substrates suitable for surface plasmon resonance reflectivity measurements. The substrates include: an SF-10 glass block, an SPR-active metallic film having a thickness in the range of about 1 nm to about 1 μm, which is adhered to the SF-10 glass block; a carbon film having a thickness in the range of about 1 nm to about 1 μm, which is adhered to the SPR-active metallic film; and a plurality of biomolecules attached to the carbon film. The substrates may include an SF-10 glass block with a thickness of between about 1 μm and about 10 cm. The substrates may include a glass prism adhered to the SF-10 glass block. The substrates may also include index matching fluid positioned between the SF-10 glass block and the glass prism. The substrates may include carbon film that comprises amorphous carbon. The substrates may include SPR-active metallic film that comprises gold. The substrates may include biomolecules that are attached to the carbon film and are configured in one or more arrays. The biomolecules may be attached to the carbon film at a density of between about $10^{10}/cm^2$ and about $5 \times 10^{14}/cm^2$.

BRIEF DESCRIPTION OF THE DRAWINGS

FIGS. 3A, 3B, 3C, 3D, and 3E taken together illustrate an example of a preparation of amorphous carbon SPR surfaces. FIG. 3A depicts a high index glass substrate. FIG. 3B depicts a glass substrate rinsed with deionized water and dried under a stream of nitrogen gas. FIG. 3C depicts a metal thin film applied to the substrate. FIG. 3D depicts an amorphous carbon thin film applied to the thin metal film by DC magnetron sputtering, followed by chemical functionalization of the carbon thin film. FIG. 3E depicts the surface functionalized with 9-decene-1-ol.

FIG. 4A depicts silanization of a glass slide. FIG. 4B depicts the corresponding functionalization of the carbon thin film depicted in FIG. 3E.

FIGS. 5A, 5B, 5C, 5D, 5E, 5F, 5G, and 5H depict the Fourier Transform Surface Plasmon Resonance (FTSPR) instrument configuration and experimental setup. FIG. 5A depicts a light beam from the external port of a Fourier transform near-infrared (FT-NIR) spectrometer focused onto an aperture and recollimated with a second lens. FIG. 5B depicts the light beam polarized with an NIR film polarizer. FIG. 5C depicts the polarized the light beam is directed onto the substrate. FIG. 5D depicts the substrate attached to a rotating stage. FIG. 5E depicts the light reflected from the substrate and focused onto an InGaAs photodiode detector. FIG. 5F depicts a Kretschmann configuration comprising a prism mounted to the substrate. FIG. 5G depicts the substrate with a layer of index matching fluid. FIG. 5H depicts an optional flow cell onto which the elements depicted in FIGS. 5F and 5G may be mounted.

FIGS. 6A, 6B, 6C, 6D, and 6E taken together illustrate one embodiment of Surface Plasmon Resonance imaging (SPRi) instrument configuration and experimental conditions. FIG. 6A depicts a collimated white light source. FIG. 6B depicts a visible film polarizer. FIG. 6C depicts the polarized light beam directed onto the substrate. FIG. 6D depicts the light reflected from the substrate refocused and passed through a narrow band pass filter. FIG. 6E depicts a CCD camera that captures light reflected from the substrate.

FIG. 7A depicts scanning angle SPR by coupling the metal film to a prism (Kretschmann configuration) to provide the proper orientation for photon-plasmon coupling. FIG. 7B depicts surface plasmon resonance imaging (SPRi) experiments employing a broad, collimated beam of light reflected at a fixed angle from the prism-coupled metal thin film.

FIGS. 9A and 9B are graphs indicating the sensitivity of SPR as a function of the thickness of carbon layers. FIG. 9A depicts percent reflectivity as a function of incident angle and carbon film thickness. FIG. 9B depicts normalized change in percent reflectivity as a function of amorphous carbon film thickness.

FIGS. 10A, 10B 10C, and 10D are examples of data from DNA-DNA binding experiments. FIG. 10A depicts an array containing 58 reference features, 17 features of Probe 1, 17 features of Probe 2, and 328 randomly generated oligonucleotide features. FIG. 10B depicts an array having shorter nucleotides, each of which contains a 10 dT spacer to provide additional distance from the surface to increase hybridization efficiency. FIG. 10C is a difference image obtained 120 seconds after Complement 1 was introduced. FIG. 10D is a difference image of the array of FIG. 10C obtained by subtracting the image taken at t=240 s from the image taken at t=120 s.

FIGS. 11A, 11B, and 11C are examples of data from DNA-protein binding experiments. FIG. 11A depicts the array design. (See paragraph 123 for details.) FIG. 11B depicts a difference image obtained 10 minutes after thrombin was introduced. FIG. 11C depicts a difference image taken 10 minutes after VFR binding buffer was introduced.

FIGS. 12A, 12B, and 12C are examples of oligonucleotide arrays synthesized on amorphous carbon and glass substrates. FIG. 12A shows the array pattern. FIG. 12B depicts fluorescence intensities when the array is fabricated on a glass substrate and hybridized with fluorescently labeled complementary oligonucleotides. FIG. 12C depicts fluorescence intensities when the array is fabricated on an amorphous carbon substrate and hybridized with fluorescently labeled complementary oligonucleotides.

(FIG. 13B).

DETAILED DESCRIPTION OF THE PRESENTLY PREFERRED EMBODIMENTS

Figure 1:
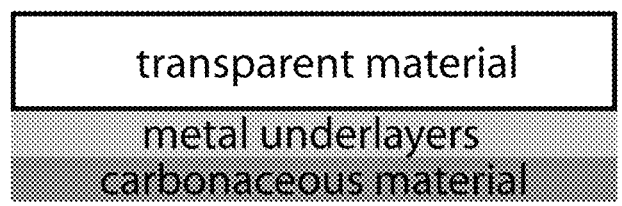
FIG. 1 illustrates one schematic embodiment of a substrate according to the present invention.

Novel carbon-on-metal thin film substrate architecture is provided, which permits the integration of surface plasmon resonance detection with photolithographically fabricated DNA arrays for the analysis of biomolecular interactions. The compositions and methods of the present invention find utility in the analysis of specific DNA-DNA, DNA-RNA, DNA-protein, and DNA-small molecule binding interactions. These new substrates can be used to determine the secondary structure of RNA molecules, and to probe the sequence-specific binding kinetics and affinity of proteins and small molecules. In addition, these new substrates can also be used as small-molecule combinatorial chemistry platforms for drug discovery applications.

Glass has become the standard substrate for the preparation of DNA arrays. Typically, glass is modified using silane chemistries to provide an appropriate functional group for nucleic acid synthesis or oligonucleotide immobilization. There may be substantial issues with the stability of these surfaces as manifested in the unwanted release of oligomers from the surface when incubated in aqueous buffers at moderate temperatures. In one aspect, the use of amorphous carbon-based substrates according to the present invention provides for in situ synthesis of oligonucleotide probes on carbon-based substrates using light directed photolithographic phosphoramidite chemistry. DNA arrays on amorphous carbon-based substrates are substantially more stable than arrays prepared on glass. This superior stability enables the use of high-density DNA arrays for applications involving high temperatures, basic conditions, or where serial hybridization and dehybridization is desired. Indeed, the increased stability of carbon-based substrates, over extended periods of time and under harsh chemical conditions, makes them an ideal surface for microarray fabrication.

Compositions are provided which can be used as substrates for SPR measurements. Provided are new surfaces that are compatible with SPR and suitable for creating high density arrays. These surfaces are more robust than their gold counterparts, making them suitable for conducting a variety of assays on the surfaces themselves, such as PCR, the INVADER assay, etc. In addition, carbon thin films are not susceptible to UV irradiation as are their gold-SAM counterparts.

This invention contemplates the use of various carbonaceous materials. "Carbonaceous" is the defining attribute of a substance that is rich in carbon. Thus, carbonaceous materials are materials that are rich in carbon. Carbonaceous layers are layers that are rich in carbon. Carbonaceous materials for the purposes of the present invention include, but are not limited to, amorphous carbon, hydrogenated amorphous carbon, tetrahedral amorphous carbon, and diamond thin films. The carbonaceous materials of the present invention may be used as materials for in situ fabrication of DNA arrays. For example, diamond deposited on silicon permits comparisons between this work and previously reported immobilizations of biomolecules. However, the principles established herein are applicable to other carbon-based materials (amorphous carbon thin films, carbon nanotubes, and carbon nanowires), and carbon-rich materials (silicon carbide).

"Amorphous carbon" refers to an allotrope of carbon that does not have any crystalline structure. As with all glassy materials, some short-range order can be observed, but there is no long-range pattern of atomic positions. Amorphous carbon is often abbreviated to aC for general amorphous carbon, aC:H for hydrogenated amorphous carbon, or to ta-C for tetrahedral amorphous carbon (also called diamond-like carbon). In technical terms, true amorphous carbon has localized π electrons (as opposed to the aromatic π bonds in graphite), and its bonds form with lengths and distances that are inconsistent with any other allotrope of carbon. It also contains a high concentration of dangling bonds, which cause deviations in interatomic spacing (as measured using diffraction) of more than 5%, and noticeable variation in bond angle. In mineralogy, "amorphous carbon" is the name used for coal, soot and other impure forms of the element, carbon that are neither graphite nor diamond. In a crystallographic sense, however, these materials are not truly amorphous, but are polycrystalline or nanocrystalline materials of graphite or diamond within an amorphous carbon matrix. The amorphous carbon of the present invention specifically includes all of the above materials. Furthermore, for purposes of the present invention, amorphous carbon includes carbon-based materials (e.g. amorphous carbon films, nanotubes, nanorods), and carbon-rich materials (e.g. silicon carbide). Amorphous carbon materials can be fabricated using a variety of thin film deposition and growth techniques, such as chemical vapor deposition, sputter deposition, and cathodic arc deposition.

The properties of amorphous carbon films vary depending on the parameters used during deposition. One of the most common ways to characterize amorphous carbon is through the ratio of $sp^2$ to $sp^3$ hybridized bonds present in the material. Graphite consists purely of $sp^2$ hybridized bonds, whereas diamond consists purely of $sp^3$ hybridized bonds. Materials that are high in $sp^3$ hybridized bonds are referred to as tetrahedral amorphous carbon (owing to the tetrahedral shape formed by $sp^3$ hybridized bonds) or as diamond-like carbon (owing to the similarity of many physical properties to those of diamond). Experimentally, $sp^2$ to $sp^3$ ratios can be determined by comparing the relative intensities of various spectroscopic peaks (including EELS, XPS, and Raman Spectroscopy) to those expected for graphite or diamond. In theoretical works, the $sp^2$ to $sp^3$ ratios are often obtained by counting the number of carbon atoms with three bonded neighbors versus those with four bonded neighbors. Amorphous carbon materials may also be stabilized by dangling-$\pi$ bonds with hydrogen. These materials are then called hydrogenated amorphous carbon. This invention also contemplates the use of all carbonaceous materials including hydrogenated amorphous carbon (aC:H), tetrahedral amorphous carbon (ta-C), as well as diamond thin films.

Figure 2:
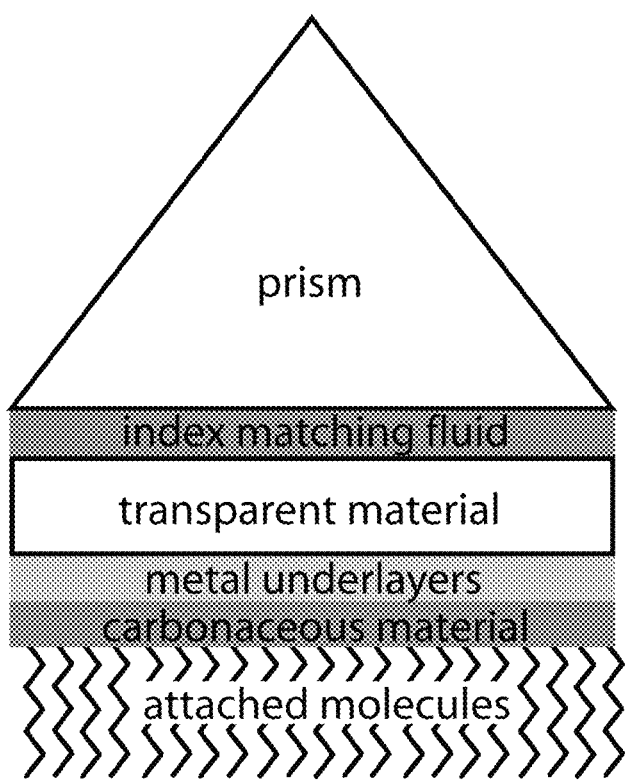
FIG. 2 illustrates another schematic embodiment of a substrate according to the present invention.

In one embodiment, amorphous carbon in the form of carbon thin-films can be applied to a wide variety of metal surfaces. One advantage brought about by use of the amorphous carbon films is that the amorphous carbon film limits oxidation of base metals and preserves SPR response in oxidizing environments like water. Suitable metal surfaces in accordance with the present invention include various noble metals, e.g. gold, silver, platinum, as well base metals such as copper, aluminum, chromium, and also various metal alloys, etc. The metal may be provided in the form of a film, preferably a thin film, with a thickness of between about 1 nm and about 1 μm. As well, the amorphous carbon may be provided in the form of a thin film. For example, a thin overlayer of amorphous carbon on traditional gold-coated SPR chips serves as an excellent substrate for covalent attachment of biomolecules while permitting the gold to undergo strong SPR resonance, which is necessary for signal transduction. Amorphous carbon substrates have superior surface chemical stability compared to traditional glass substrates, thus opening the door to performing assays under higher temperatures and harsher chemical conditions than is currently possible. FIG. 1 illustrates one embodiment of the substrates of the present invention. Shown in FIG. 1 is a substrate that includes layered: carbonaceous material; metallic layer adhered to the carbonaceous material, and transparent material adhered to the metallic layer. FIG. 2 illustrates another embodiment of the substrates of the present invention. Shown in FIG. 2 is a substrate that includes layered: carbonaceous material; metallic layer adhered to the carbonaceous material; and transparent material; and a transparent prism adhered to the transparent material. Also shown in FIG. 2 is an optional layer of index matching fluid, which is positioned between the transparent material and the transparent prism. Index matching fluids are used to reduce or eliminate reflective losses to light at interfaces. The refractive index of the fluid is chosen to match that of the dielectric materials it is placed between, thus making the interface transparent to the light. In one embodiment, Cargille Series M (refractive index 1.7200) index match fluid is placed between an SF 10 glass prism and the SF 10 glass substrate. Light passes through the prism, fluid and substrate and impinges on the metallic layer adhered to the glass with little or no reflective loss at the interface between the prism and the substrate.

"Biomolecules" for the purposes of the present invention include, but are not limited to, single and double-stranded oligonucleotides, DNA, RNA, proteins, protein fragments, amino acids, peptides, aptamers, antibodies, antigens, lectins, carbohydrates, transcription factors, cellular components, cellular surface molecules, viruses, virus fragments, lipids, hormones, vitamins, and small molecules such as drugs. The biomolecules may be attached directly to the carbonaceous material, which may be a carbonaceous layer or a carbon thin film. Alternatively, or in addition, the biomolecules may be attached to the carbonaceous material via a number of chemical linker and spacer moieties. This invention contemplates the direct attachment of biomolecules to the carbonaceous material; adsorption of biomolecules to the carbonaceous material; attachment of biomolecules to the carbonaceous material via a linker; adsorption of biomolecules to the carbonaceous material via an intermediate layer, e.g. poly(lysine) or dextran; or attachment of biomolecules to the carbonaceous material through bioconjugation (e.g. avidin-biotin or antigen-antibody).

This invention contemplates a plurality of biomolecules attached to the carbonaceous material. The attached biomolecules may be configured in one or more arrays. The attached biomolecules may differ from each other. Alternatively, the attached biomolecules may be identical to each other. As well, combinations of different and identical molecules may be attached to the carbonaceous material.

In one aspect, DC-sputtered amorphous carbon and clean gold surfaces are a powerful example of the SPR-compatible thin films of the present invention. For example, this invention contemplates to overlay the standard SPR gold thin film with a thin (e.g. 1 nm to 1 μm) layer of amorphous carbon. The carbon layer is sufficiently thin that it only occupies a minor fraction of the SPR-active sensing volume. The carbon may be deposited in a variety of ways, e.g. by DC sputtering, which is a gentle process effected at ambient temperature, and thus does not damage the underlying metal film. Versatile chemistries for the modification of carbon surfaces, based upon the formation of carbon-carbon bonds, are known in the art (Strother et al., 2002, *Langmuir* 18: 968-971; Yang et al., 2002, *Nat. Materials* 1: 253-257; Knickerbocker et al., 2003, *Langmuir* 19: 1938-1942; Sun et al., 2006, *Langmuir* 22: 9598-9605; Phillips et al., 2008, *Nucl. Acids Res.* 36: e7). The high stability of these carbon materials, in conjunction with the stable carbon-carbon bonds used for biomolecule attachment, make this an extraordinarily powerful and versatile platform for molecular interaction analysis on surfaces.

The use of carbon substrates for SPR measurements provides numerous advantages, for example with respect to opening up many new possibilities in molecular interaction analysis. First, these substrates can be used in the light-directed fabrication of high density DNA arrays analogous to Affymetrix or Nimblegen DNA chips. This is not possible on a gold thin film due to the UV-mediated oxidation of the gold-thiol bonds utilized in surface modification. Thus, it is possible for the first time to use label-free detection in conjunction with high density DNA arrays, opening up the world of parallel large-scale analysis of DNA-DNA, DNA-protein, peptide-protein, small molecule-protein, and protein-protein interactions without a requirement for labeling. This elimination of the need for labeling is important for at least two reasons: first, when, for example, studying a single purified protein, it eliminates the need to chemically modify a potentially delicate biomolecule and the concomitant concern that the label might alter or modify the biomolecule's activity or behavior; second, and probably more importantly, it means that biomolecules in complex mixtures such as nuclear extracts can be studied directly without having to purify them and attempt to label them in the mixture (an approach that does not work well due to the complexity and heterogeneity of the mixture and difficulty in removing fluorescence reaction by-products present in high concentration). Second, the extraordinary chemical stability of the carbon surfaces and associated attachment chemistries allows harsh chemical conditions to be employed (strong acids and bases, oxidants and reductants, solvents, heat, light, and so on), meaning that combinatorial chemistry synthetic methods for small molecule library synthesis are viable. This also opens up a new world of possibilities for fabrication of small molecule arrays to study molecular interactions with biomolecules of interest. Just as for the DNA arrays, this eliminates the burden and concerns associated with labeling of particular biomolecules of interest and makes possible the querying of complex mixtures. A third advantage of the carbon:metal substrates is the compatibility of these substrates with mass spectrometric analysis. The glass substrates generally utilized in DNA array fabrication are not electrically conductive, like most planar substrates employed in combinatorial chemistry applications. This means they do not work well as substrates for MALDI analysis because of charge build-up on the surface in the ion source. MALDI analysis works very well from the carbon:gold substrates, for either intact proteins or peptide digests. In addition, these substrates perform similarly to DIOS, i.e. Direct Ionization on Silicon (Thomas et al, 2002, *Proc. Natl. Acad. Sci. USA* 98: 4932-9437) substrates for matrix-free laser desorption analysis for peptides of mass up to ~1500 Daltons. This capability significantly increases the power of the carbon:metal thin film platform, as not only is it possible to do detailed quantitative and kinetic analyses of surface binding reactions, it is also possible to identify, by peptide mass mapping or tandem MS, unknown binding partners that bind to molecules on the surfaces. This is a terrific advantage for applications in which one seeks to elucidate molecular interactions occurring in complex mixtures such as nuclear extracts.

Figure 7A:
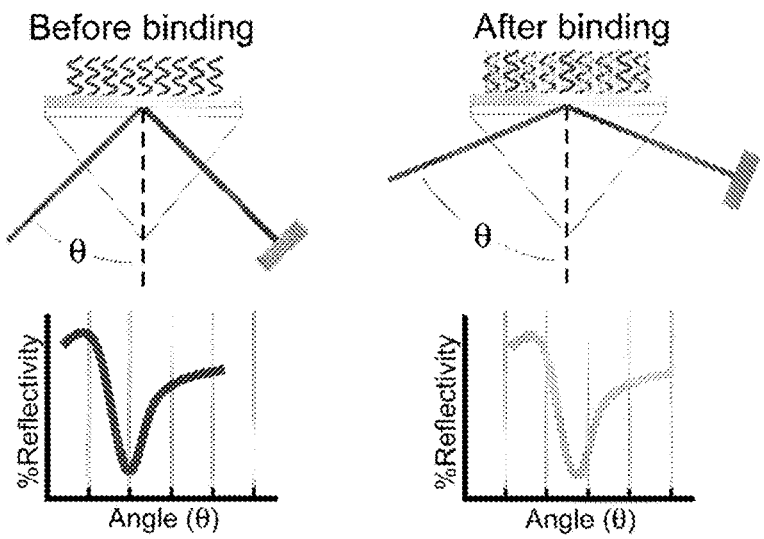
FIGS. 7A and 7B depict typical surface plasmon resonance (SPR) experiments.
Figure 7B:
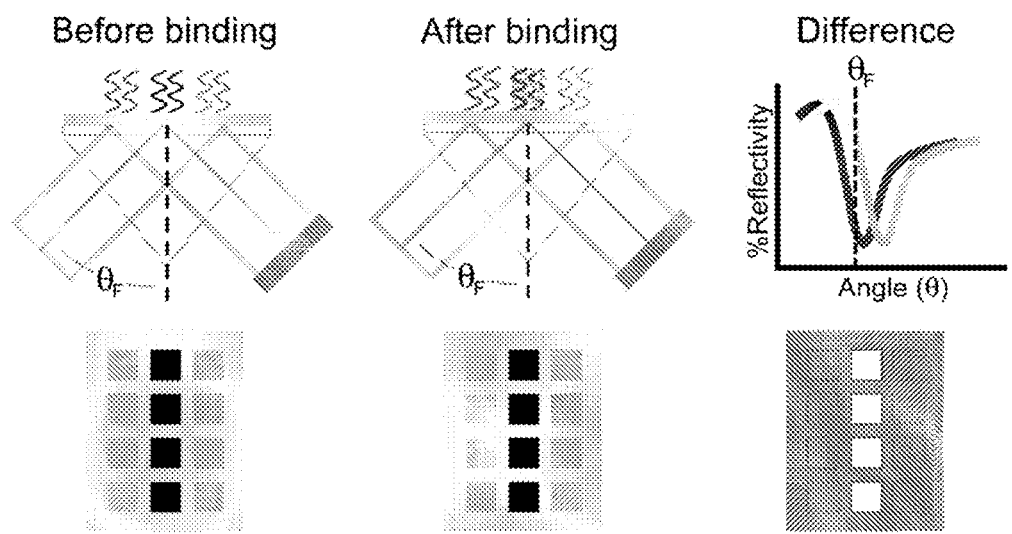

Surface plasmon resonance (SPR) measurements typically utilize one of two configurations: either the reflectivity is monitored as the angle is scanned (FIG. 7*a*), or a fixed-angle is employed, which allows imaging of differences in refractive index across a surface (FIG. 7*b*). This invention contemplates the use of a variety of electromagnetic waves for surface plasmon resonance measurements. These electromagnetic waves include the following regions of the electromagnetic spectrum: UV (ultraviolet), V is (visible), NIR (near infrared), IR (infrared), and FIR (far infrared).

Various aspects of SPR sensor technology have been developed in recent years (Homola et al., 1999, *Sensors and Actuators B* 54: 3-15). A variety of SPR instruments have been commercialized for bioaffinity sensing, and these are widely used for the characterization of surface-based binding processes. For example, U.S. Pat. No. 5,351,127, incorporated herein by reference, discloses surface plasmon resonance measuring instruments; U.S. Pat. No. 7,271,914 B2, incorporated herein by reference, discloses a biomolecular sensor system utilizing a transverse propagation wave of surface plasmon resonance. U.S. Pat. No. 6,798,521, incorporated herein by reference, discloses a robust integrated surface plasmon resonance sensor.

Imaging with SPR has been used for looking at native structures and for performing binding experiments on surfaces engineered with patterns of chemical functionalities. Studies of biomolecular interactions have been performed with surface plasmon resonance imaging (SPRi) on various types of patterned surfaces (Wegner et al., Surface Plasmon Resonance Imaging Measurements of DNA, RNA and Protein Interactions to Biomolecular Arrays. *In Protein Microarray Technology*, Wiley-VCH: 2004; p 107-129). Such patterning to create an array of differently functionalized spots on a metal thin film enables built-in control experiments and/or multiplexed measurements simultaneously on the same surface. One consideration with imaging applications such as microscopy or analysis of patterned arrays is the minimum feature size that can be resolved. The lateral resolution of SPRi depends upon the propagation length of the surface plasmon oscillations at the interface, which in turn depends upon the complex dielectric function of the metal as well as radiative damping; a resolution of ≤5 µm has been obtained. The ability to photopattern high density arrays on the new carbon-on-metal films described herein will enable SPRi experiments that push this limit, having more than one million features per square centimeter.

A significant limitation of SPR is the requirement for the binding process to occur on a metal thin film. There are a number of different metal thin films (gold, silver, copper, aluminum, and others) capable of supporting surface plasmons in the near infrared and visible regions of the electromagnetic spectrum (Mitsushio et al., 2006, *Sensors and Actuators A* 125: 296-303. Ordal et al., 1983, *Applied Optics* 22: 1099-1120.) However, two factors have restricted surface plasmon resonance-based detection primarily to gold: first, most metals are subject to oxidation and/or other reactions upon exposure to aqueous solutions; and second, a versatile chemistry for attaching sulfur-containing ligands to gold surfaces has been developed and well-characterized. This chemistry, enabling the direct attachment of ligands to the gold surface, or attachment via an intermediate self-assembled monolayer, has made possible the routine analysis of aqueous binding processes to immobilized molecules at near-neutral pH values and moderate temperatures. However, the susceptibility of the gold-sulfur bond to oxidation and photodecomposition has prevented SPR sensing from finding utility in important areas such as on-surface combinatorial chemistry (due to the harsh chemical conditions employed) and photolithography (due to the adverse effects of ultraviolet radiation on the gold-sulfur bond).

Amorphous carbon, SPR-compatible substrates for high density microarray fabrication and analysis are provided. Methods are also disclosed which provide for the fabrication of such substrates. Provided are methods for the development of a lamellar structure in which a thin layer of amorphous carbon is deposited onto a surface plasmon-active metal thin film. The utility of this multilayered substrate is demonstrated by its ability to support photolithographic synthesis of oligonucleotide arrays (Singh-Gasson et al., 1999, *Nature Biotechnology.* 17: 974-978) which are then employed for the analysis of biomolecule binding processes with SPR imaging. The in situ fabrication of oligonucleotide arrays utilizing photochemically protected oligonucleotide building blocks is not possible with traditional (metal-only) surface plasmon resonance substrates due to the extended exposure to ultraviolet light and oxidizing chemical conditions. However, the substrates of the present invention open many such possibilities for the fabrication of molecular arrays and large-scale analysis of their binding interactions utilizing SPR spectroscopic methods.

While many allotropes of carbon are available, amorphous carbon is the only allotrope that can easily form reproducible thin films at room temperature. By applying a carbon layer much thinner than the typical plasmon penetration depth, the SPR effect is only modestly perturbed by its presence. Carbon surfaces are readily modified with biomolecules of interest using a well-developed and robust chemistry, based upon the attachment of alkene-containing molecules to the substrate through the light-mediated formation of a carbon-carbon bond (Strother et al, 2002, *Langmuir* 18: 968-971. Sun et al, 2006 *Langmuir* 22: 9598-9605). The high intrinsic stability of the carbon material and of the carbon-carbon bond to the linking molecules makes this material impervious to reaction conditions that would otherwise destroy gold self-assembled monolayers. Biomolecule arrays on modified carbon surfaces (Yang et al., 2002, *Nature Materials* 1: 253-257. Sun et al., 2006, *Langmuir* 22: 9598-9605) have also shown superior stability over their gold analogs.

The chemical robustness of the amorphous carbon overlayer affords synthetic possibilities not previously available with gold substrates. For example, in situ photolithographic oligonucleotide array synthesis requires a substrate that is planar, easily functionalized, and robust enough to withstand prolonged exposure to bases, oxidizing agents, and ultraviolet light. To determine the minimum thickness of functionalized amorphous carbon needed to support the chemical requirements of in situ oligonucleotide array synthesis, substrates of varying amorphous carbon thickness (2.5-20 nm) were exposed to the reaction conditions needed to synthesize an 18-nucleotide sequence. The minimum thickness of the amorphous carbon needed to consistently support the array fabrication process is 7.5 nm. It is contemplated that the carbon thin-films of the present invention have a thickness in the range of about 1 nm to about 1 μm.

Provided herein is a new system for molecular interaction analysis. The ability to fabricate a large number of oligonucleotide features on a single, SPR-compatible array opens many new possibilities for probing important biomolecular interactions. These include DNA-DNA, DNA-RNA, DNA-protein, and DNA-small molecule interactions.

Compositions and methods for functionalization of surfaces in order to bind various molecules are provided. In particular, surfaces may be functionalized so that they can bind biomolecules. The compositions and methods may be used to attach (immobilize) molecules with a relatively high density ($10^{10}/cm^2$ and about $5\times10^{14}/cm^2$) onto surfaces that are suitable for surface plasmon resonance (SPR) reflectivity measurements (i.e. are SPR-active). Assays may then be conducted to detect, in a label-free manner, binding of other molecules to the immobilized molecules.

A general platform for the multiplex analysis of bioaffinity interactions is provided. This platform may be used for the analyses of particularly important biological processes. In one aspect, the sensing platform combines three powerful capabilities: surface plasmon resonance (SPR) imaging for multiplexed label-free measurements of surface binding in an array format; a novel SPR-active substrate consisting of a rugged carbon thin-film overlayer on an SPR-active metal thin film with versatile and highly stable attachment chemistries based upon carbon-carbon bond formation; and mass spectrometric analysis capability to identify unknown ligands binding to the surface. The combination of SPR imaging, the rugged and chemically versatile carbon surfaces and attachment chemistry, and mass spectrometric capability provides this system with unprecedented utility for analysis of bioaffinity interactions.

It should be apparent that it is possible to vary the carbon-over-metal thin film substrates for different applications, vary the conditions and film parameters for metal and carbon deposition; vary the attachment chemistries for proteins, DNAs, and small molecules. For example, amorphous carbon coated SPR substrates that employ gold as the active metal film exhibit about 70% of the sensitivity of conventional bare gold SPR substrates. However, the sensitivity may be changed by employing other SPR-active metals. Metals other than gold (Cu, Ag, Al) are attractive because they are known to offer improved sensitivity and spatial resolution in their non-oxidized form. Up to this point, other metals have found little utility in SPR binding assays because of their rapid oxidation under ambient conditions. The use of amorphous carbon over-layer attenuates or blocks metal oxidation. Therefore, metals other than gold may be utilized to increase SPR detection sensitivity.

In one example, substrates suitable for SPR reflectivity measurements may be fabricated in a process involving depositing of a metal layer in the form of a thin film onto a dielectric material with a high index of refraction. An example of dielectric material with a high index of refraction is SF10 Glass (n=1.7200, 800 nm light), with a wavelength range of 400 nm-2400 nm and an angular dispersion of 2° 58'25" (Schott Glass, Mainz, Germany). Other types of suitable dielectric materials with a high index or refraction include other suitable types of glass (BHK 7, float glass, quartz, etc.). The metallic layer may be deposited onto the transparent member using thermal and/or electron-beam evaporation, electrochemical plating, and spray coating methods. An amorphous carbon thin film is then applied, e.g. by DC sputtering, or by DC sputtering, laser ablation techniques, or chemical vapor deposition methods. The thickness of each thin film may be confirmed using atomic force microscopy (AFM). The thickness of both the metal and amorphous carbon thin films is then optimized to achieve the maximum signal from each surface. Prior work on gold-containing substrates provides a reasonable thickness range to work with (35-55 nm) for other metals that may be used according to this invention, including Ag, Cu and Al. These metals support the generation of surface plasmons in the visible/near-infrared region of the electromagnetic spectrum. It is thus possible to prepare a series of substrates with various metal and amorphous carbon thicknesses and then use scanning angle SPR imaging to determine the maximum achievable sensitivity with each combination.

The thickness of the metal can be instrumentally examined, e.g. using a Fourier-transform surface plasmon resonance (FTSPR) obtained from GWC Technologies (Madison, Wis.). This high sensitivity instrument is capable of detecting changes in film thickness of <0.1 nm (Frutos et al., 1999, *Anal. Chem.* 71: 3935-3940), and can also detect the binding of small molecules to immobilized proteins. The GWC FTSPR has the greatest dynamic range of any commercially available SPR system. It operates from ~11,000 to 6,000 cm$^{-1}$ over 40-70° incident angles and captures quantitative data for both major and minor surface changes. It is thus possible to determine the optimum metal thickness for various metal films. The thinness of the amorphous carbon layer that can be practically employed can be determined by the film adhesion, which in turn depends upon the particular metal employed. The minimum thickness of amorphous carbon that permits good adhesion yields the highest SPR sensitivity. The minimum film thickness that withstands the preparation and application conditions for each assay can be determined and employed for subsequent experiments.

The process for experimentally determining the maximum achievable sensitivity requires obtaining angle dependent SPR response for a broad range of light wavelengths. In one aspect, a Fourier transform surface plasmon resonance (FTSPR) system may be used to obtain this data. Fourier transform surface plasmon resonance instruments are generally known in the art. U.S. Pat. No. 6,330,062, incorporated herein by reference, discloses a particular FTPSR that can utilize the amorphous carbon-gold substrate of the present invention. U.S. Pat. No. 5,629,213, incorporated herein by reference, discloses a biosensor for use in SPR that can also utilize the amorphous carbon-gold substrate of the present invention. U.S. Patent Application Publication No. 2003/0017579, incorporated herein by reference, discloses methods for fabricating microarrays using parallel microfluidic channels on chemical-modified metal, carbon, silicon and/or germanium surfaces that can utilize the amorphous carbon-gold substrate of the present invention. U.S. Patent Application Publication No. 2005/0048501, incorporated herein by reference, discloses methods and instruments for detecting DNA using complementary RNA probes and an enzyme that attacks and hydrolyzes the RNA probes only when it has hybridized with DNA, where the test may utilize SPR and the amorphous carbon-metal film substrate of the present invention. U.S. Patent Application Publication No. 2004/0201848, incorporated herein by reference, discloses a portable SPR device that can utilize the amorphous carbon-gold substrate of the present invention. U.S. Pat. No. 6,127,129, incorporated herein by reference, discloses a process to construct multi-component biomolecule or cellular arrays suitable for use in SPR that can also utilize the amorphous carbon-gold substrate of the present invention. U.S. Patent Application Publication No. 2006/0066249, incorporated herein by reference, discloses substrates, instruments and methods for SPR that can utilize the amorphous carbon-gold substrate of the present invention. U.S. Pat. No. 6,849,397, incorporated herein by reference, discloses instruments and methods for detecting unlabeled nucleic acids in a taxa, species, and organelle-specific fashion, using SPR that can also utilize the amorphous carbon-gold substrate of the present invention. U.S. Pat. No. 7,067,322, incorporated herein by reference, discloses methods for making fusion protein arrays on metal substrates for use in SPRi.

The substrates of the present invention may be used in various known SPR devices, with SPR detection systems configured in a variety of formats, e.g. in those devices using a common geometrical setup of the so-called Otto configuration, and the so-called Kretschmann configuration. An alternatively suitable optical setup for SPR detection is the so-called grating-coupled configuration. In this configuration, the substrate consists of a periodic modulated surface that diffracts the incident light to various orders. The grating surface is coated with a metal film and SPR occurs at a suitable incident light angle of incidence, wavelength, and polarization. Changes in the SPR response are detected by measuring the reflected light intensity.

The carbon substrates (e.g. in the form of films or layers) of the present invention may be functionalized in a variety of ways known in the art, e.g. using the photochemical method set forth in U.S. Pat. No. 6,569,979, incorporated herein by reference. An alkene molecule may be covalently attached to a carbon substrate through the use of a UV-light mediated reaction. Carbon surfaces can be readily functionalized with a range of primary alkene derivatives by UV irradiation resulting in a loading density of ~5×10$^{12}$ molecules/cm$^2$ (Thoms and Butler, 1995, *Surface Science* 328: 291-301; Thoms et al., 1994, *Applied Physics Letters* 65: 2957-2959). This allows for the incorporation of masked (chemically protected) nucleophiles or electrophiles for subsequent syntheses from the support. The loading level is typically similar to that used in array synthesis on planar cellulose supports (50-500 nmol/cm$^2$). This allows for straightforward compound characterization and quantification per spot. In one example, reactive surfaces are prepared by placing a small drop of a neat alkene on the surface and then applying a quartz cover-slip. The cover slip causes the solution to spread evenly over the carbon surface. The substrate is then exposed to ultraviolet light from a low-pressure mercury lamp ($\lambda$max=254 nm), which initiates the radical-mediated coupling of the alkene to the surface. To optimize the attachment chemistries, reactions may be monitored using a surface characterization methods such as X-ray photoelectron spectroscopy, polarization modulated Fourier transform infrared reflection absorption spectroscopy, ellipsometry, and contact angle measurements.

Other reported chemistry includes a scheme for attachment of functionalized organic molecules to polycrystalline diamond films (Strother et al., 2002, *Langmuir* 18: 968-971). Organic molecules having suitable protecting groups are attached and subsequently deprotected after attachment to the surface. Such functional groups may serve as starting points for further chemical modifications.

The stability of amorphous carbon substrates during light-directed microarray synthesis makes them an outstanding candidate for surface-based synthetic chemical processes. The present invention contemplates functionalization of planar carbon substrates for spatially addressed small molecule synthesis. Shown in FIG. 17 is a general schematic of spatially-addressed small molecule synthesis on amorphous carbon supports.

Figure 17:
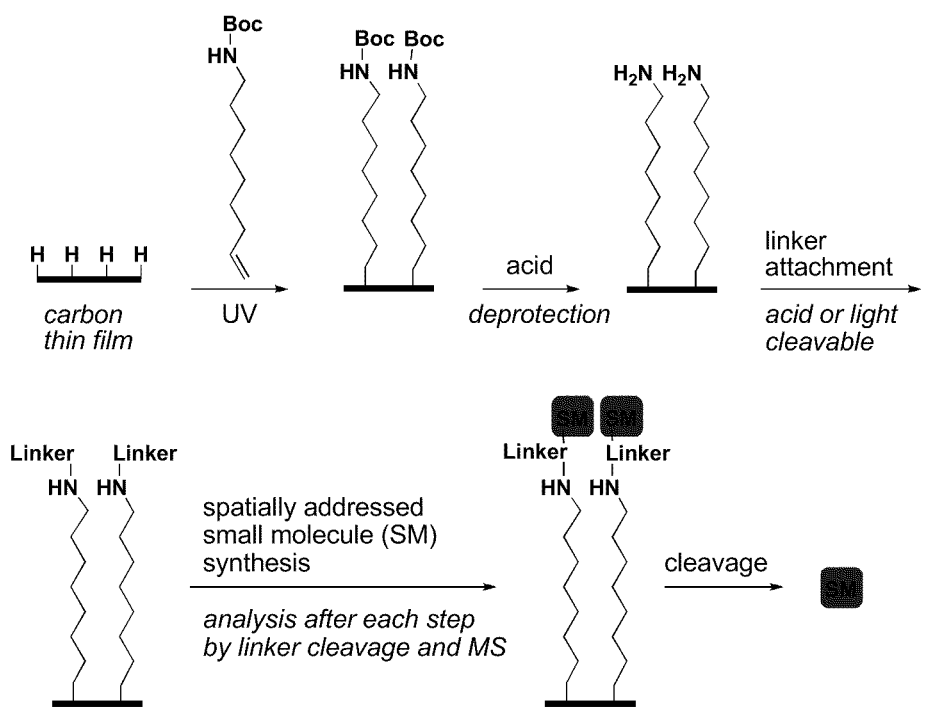
FIG. 17 illustrates the general schematic of spatially-addressed small molecule synthesis on amorphous carbon supports.

An alkene bearing a protected primary amine is shown in FIG. 17 as a representative example of substrate functionalization. After deprotection of the amine, standard chemical linkers (all commercially available) can be attached to the support via amide bond formation. Thereafter, small molecule synthesis can commence in a spatially addressed manner through delivery of reagents to specific locations on the surface. Small amounts of reagent volumes (1-10 μL) can be applied using standard micropipettes. Excess reagents may be used (5-10 equivalents) to push reactions to completion, as is typically done in standard solid-phase organic synthesis. The substrate can be heated in a microwave synthesis reactor or in a laboratory oven when necessary. Substrate loadings, reaction efficiencies and conversion to products are monitored by cleavage of compounds from test spots using mild acid and examination of the resulting isolate by LC-MS. Calibration curves (created from UV HPLC analyses) may be used for compound quantification, as has been done for reaction monitoring in array syntheses (Blackwell, 2006, *Current Opinion Chem. Biol.* 10: 203-212).

One potential concern is that it may be difficult to confine the reactions to array features. This may be addressed by patterning alkenes of contrasting hydrophobicity, using a physical mask, to confine the reactants and their solvents to the features. A procedure originally developed for photopatterning SAMs on gold by may be adapted for this purpose (Gillmor et al., 2000, *Langmuir* 16: 7223-7228). The procedure begins by obtaining a reusable metalized quartz mask with transparent features of specified size, each of which pass UV light. This mask is placed on top of the substrate, with the metallic side closest to the carbon. UV light directed through the mask illuminates only the regions of the chip corresponding to the array features. The light initiates a reaction between the carbon and an alkene bearing a reactive function group (e.g. a protected amine). Once the reaction is completed, the mask is removed and the substrate is rinsed. A second alkene bearing a blocking group (e.g. perfluorinated alkane or polyethylene glycol (PEG)) is applied to the surface of the carbon, which is then covered with a quartz cover slip. The surface is again exposed to UV light, which causes the alkene to react to the carbon in the interstitial region between the features.

Alternatively, a surface could be patterned using an optical mask generated with a maskless array synthesizer in exchange of a physical mask.

In one example, an array of small molecules may be fabricated on a carbon support using a plurality of organic chemical reactions. Such reactions may include: Grignard reactions (strong base), catalytic hydrogenation (high pressure), Wittig reactions (strong base), sigmatropic rearrangements (e.g., Claisen and Cope; high temperature), aldol reactions (strong base), and various oxidation/reduction reactions (harsh, metal-based reagents). Reactions that are found to be compatible with carbon-based supports may be utilized for the design of structurally diverse small molecule arrays.

If desired, oxidation of sensitivity optimized metal:amorphous carbon substrates can be measured following exposure to oxidizing conditions. Oxidation of metal thin films introduces significant shifts and broadening of the SPR profile. Oxidation conditions can range from exposure to water, buffered solutions common in biological reactions, and solutions containing oxidizing agents (e.g. hydrogen peroxide, Dess Martin reagent) commonly used in small molecule synthesis.

The present invention contemplates the use of surface chemistry to reduce non-specific binding. Unmodified carbon surfaces are quite hydrophobic and thus can be prone to non-specific binding of some proteins. Surface modification with either polyethylene glycol or fluorinated molecules substantially blocks some forms of non-specific binding. Thus, the use of fluorinated molecules provides a good surface for preventing protein adsorption. These reagents are also commercially available and are effective at low surface densities. In one embodiment, the photolithographic patterning of alkenes may serve a dual purpose, to confine reactants and solvents to individual features, and to prevent non-specific binding of protein. As an example, a reaction involving an amine terminated feature that employs hydrophilic solvents will be confined to the feature by surrounding it with hydrophobic fluorinated alkenes, which will also reduce or eliminate non-specific binding of proteins. In another example, it is possible to photodeprotect the region of the substrate adjacent to the features to generate hydroxyl groups, which can then be chemically coupled to fluorinated alkanes or polyethylene glycols. A major advantage to this approach is that the patterning is straightforward using a maskless array synthesizer and also that the reactions are carried out with existing reaction cells and fluidics.

In some examples, there may be a number of functional groups that remain unreacted following attachment of protein to the substrate. These unreacted groups may play a large role in non-specific adsorption of dsDNA. Carboxylic acid modified features may exhibit less non-specific DNA binding because unreacted acid groups on the surface will naturally repel free dsDNA sequences through charge-charge repulsion whereas unreacted amine groups will naturally attract dsDNA. Non-specific adsorption to unreacted aldehydes will be in the form of Van der Waal's (including polarization and London dispersion) interactions. It may possible to mix polyethylene glycols and perfluorinated compounds with the reactive molecules of the feature as well as to additionally use one or more global blocking agents such as salmon sperm DNA and BSA to reduce or eliminate non-specific binding to aforementioned levels. Salmon sperm DNA and BSA can be used so long as they are applied prior to obtaining the background (pre-binding) image.

In one aspect, patterned test surfaces to measure non-specific binding of proteins may be prepared. In this case, un-terminated (bare carbon) features are surrounded by either fluorinated alkenes or polyethylene glycols. Substrates are placed in an SPR imager and solutions of protein delivered to the array surface. The difference in reflectivity between the modified and unmodified regions is a direct measure of protein adsorption. The type and length of blocking group may then be systematically varied to minimize non-specific adsorption.

To reduce non-specific adsorption within a feature, application of mixtures of small-molecule reactive alkenes with fluorinated alkenes is used. The ratio between reactive alkenes and fluorinated alkenes may be optimized to promote highest degree of specific binding between proteins and immobilized small molecules. Non-specific adsorption is dependent on the chemical nature of the immobilized small molecule, the number of unreacted alkenes and the widely varying nature of proteins. If desired, significant binding results may be validated in cell-based assays, which may serve to eliminate false positives.

In one embodiment this invention contemplates characterization of protein binding to immobilized small molecules. An important step in the development of the small molecule array platform as a tool for analysis of protein-ligand binding is the evaluation of the relationship between surface binding and solution binding behavior. In the ideal case, the surface would not perturb binding; however, in practice it could exert a variety of effects. Accordingly, a targeted array of ligands may be prepared. A solution of protein (10 nM) is then incubated with the array and the binding is monitored by SPR, looking for qualitative agreement with the known binding properties. In cases where surface binding is not in accord with the expected results from solution binding experiments, the nature of the linker (length, hydrophobicity, flexibility, etc.) may be systematically varied to optimize binding. The characterization of the small molecule arrays may further include verification that surface-immobilized native and non-native molecules bind specifically to their target proteins. Binding of protein from the buffered cell lysate is monitored by SPR imaging.

Protein identification is performed by on-substrate digestion with trypsin followed by elution and LC/MS/MS.

In one aspect this invention brings the power of protein identification methods to work in conjunction with array technology and SPR imaging detection, where mass spectrometry can be used to identify unknown proteins that are bound to nucleic acid or small molecules on the carbon: metal thin film substrates. Thus, the present invention contemplates measuring protein binding to substrates using SPR followed by protein identification by mass spectrometry.

There are at least three approaches to the mass spectrometric-based identification of molecules captured on substrates: direct laser desorption for small molecules and peptides; matrix-assisted laser desorption for peptides and proteins; and on-substrate tryptic digestion followed by elution for protein identification by tandem mass spectrometry of the tryptic peptides. In some aspects, the present invention also contemplates the synergistic use of two or more of these mass spectrometric analyses.

Substrates for protein arrays may be fabricated using amine-, carboxylic acid-, and/or aldehyde-reactive substrates for protein immobilization. For example, proteins may be covalently immobilized on the surface using standard coupling chemistry procedure. Free amine moieties on the proteins may be reacted with carboxylic acid groups on the surface (and vice versa) using standard carbodiimide coupling chemistries. Alternatively, coupling of surface-immobilized aldehydes with free amines on proteins using Schiff-base chemistry may be used (Peelen and Smith, 2005, *Langmuir* 21: 266-271). Both reactions can be monitored in situ by SPR. This is accomplished by placing the reactive substrate in the SPR imager cell, adding protein in the presence of coupling reagents, and noting the changing reflectivity of the surface over time. Reaction completion corresponds with a cessation of reflectivity change. Coupling of protein to the surface can be further characterized by labeling the surface-immobilized proteins with fluorescent dye and examining the substrate with a fluorescence scanner. For example, such measurements can routinely be performed using a UC4×4 four-color laser scanner with 1 μm resolution. Proteins immobilized on the surface may be quantified by standard SPR methods that employ measured changes in refractive index at the surface (Shumaker-Parry and Campbell, 2004, *Anal. Chem.* 76: 907-917; Stenberg et al., 1991, *J. Colloid and Interface Science* 143: 513-526; Rogers et al., 1999, *Anal. Biochem.* 266: 23-30).

The present invention contemplates the characterization of DNA binding to immobilized proteins. Binding between immobilized protein and solution phase dsDNA may be observed by SPR imaging. When optimizing the methods of the present invention, qualitative agreement is sought with the known binding properties. In cases where surface binding is not in accord with the expected results from solution binding experiments, the nature of the linker (length, hydrophobicity, flexibility, etc.) may be systematically varied to optimize binding. Specific binding may also be improved by reducing non-specific binding of DNA.

In one aspect the present invention contemplates light-directed synthesis of oligonucleotides. Oligonucleotide synthesis requires a free hydroxyl group as the point of attachment. Hydroxyl-terminated surfaces may be prepared using methods known in the art (Phillips et al. 2008, *Nucleic Acids Res.* 36: e37), and according to the schemes outlined in FIGS. 4 and 3. Characterization of the hydroxyl-density and stability of attachment can be confirmed by fabricating and testing DNA arrays. In general, good hybridization and protein binding may occur at an intermediate hydroxyl density ($10^{12}$ molecules/cm$^2$) rather than at high-density ($10^{14}$ molecules/cm$^2$) because of issues with steric hindrance in binding. Therefore, hydroxyl terminated substrates can be prepared using a series of UV exposure times, to vary the surface hydroxyl density. Hybridization density (a measurement of the number of complementary oligonucleotides that bind to the surface) can be measured and used to assess performance. In one example, hybridization density is measured by incubating the substrate with fluorescently tagged oligonucleotide complement followed by a quick rinse to remove non-bound complements. The bound oligonucleotide complements are then eluted from the surface with a known volume of 8M urea. The concentration of the complement is then determined by measuring the fluorescence of the solution and comparing it against fluorescence from known concentrations of the complement.

Because nucleic acids will not attach efficiently to untreated glass slides and because the uniformity of the slide surface is critical to the quality and reproducibility of arrays, glass slides are typically modified using silane chemistries. However, the susceptibility of siloxane linkages to hydrolysis under standard conditions and the increase in the rate of hydrolysis at elevated temperatures and at basic conditions is well known. Typically, silanization is used to introduce aldehyde, amino, or poly-lysine groups to the surface. A similar flexibility in surface functionality can be achieved on carbon substrates by using an alkene containing the desired functional group. The carbon-carbon covalent bonds within the carbon substrate and between the substrate and the linker moiety are not susceptible to hydrolysis. The high stability of DNA arrays fabricated on carbon substrates, compared to their glass counterparts, reflects this fact. This increased stability of DNA arrays is important for any application where it is desirable to employ higher temperatures, extended reaction times, or basic pH conditions. Such applications include solid-phase-PCR and surface invasive cleavage reactions. The stability of carbon substrates also permits their use in serial hybridization-dehybridization cycles. Arrays prepared on glass exhibit a loss of fluorescence with each subsequent chemical dehybridization cycle while the fluorescence signal obtained from carbon substrates does not follow this trend.

Using the compositions and methods of the present invention, in situ photolithographic synthesis of DNA arrays on non-glass substrates is readily achievable. These arrays offer superior stability compared to their glass counterparts under a variety of conditions. This technology enables both the repeated reuse of DNA arrays, and the use of DNA arrays for applications involving high temperatures and extremes in pH not previously accessible.

In one aspect, when synthesizing oligos in situ, the parameters for optimization of a maskless array synthesizer (MAS) performance are: phosphoramidite concentration and coupling time; photo-deprotection conditions (UV light dose and pulse sequence, exposure solvent and solvent mixing); activator type; oxidizer strength and frequency of application, and final deprotection conditions. These parameters may be varied systematically, beginning with values obtained for optimal synthesis on glass, and the resultant surfaces will be characterized by hybridization density.

This invention contemplates the use of chemical-based cleavage methods to release oligonucleotides from the surface. By introducing a linker molecule that is both robust against in situ DNA synthesis conditions (UV light, oxidizers, acids, etc.) and selectively cleavable, it is possible to collect and pool synthesized DNA. One such linker molecule is the commercially available chemical phosphorylation reagent (3-(4,4'-dimethoxytrityloxy)-2,2-dicarboxy-ethyl]propyl-(2-cyanoethyl)-(N,N-diisopropyl)-phosphoramidite (Glen Research, Sterling, Va.).

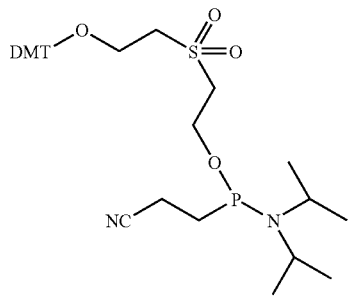

By coupling this reagent at the 3' end of the growing oligonucleotide chain, a sulfonylethyl group is introduced which, when treated with ammonium hydroxide, will release the synthesized DNA into solution. This method accomplishes simultaneous DNA base deprotection and oligonucleotide release from the substrate. Ammonium hydroxide is then removed by vacuum.

In one aspect this invention contemplates characterization of protein binding to immobilized DNA. The binding between immobilized DNA and solution phase proteins may be observed by SPR imaging. Surfaces with DNA will be prepared for these experiments by exposing the photolithographically fabricated oligonucleotide array to complementary oligonucleotides and permitting them to hybridize. The proteins employed in this analysis may be from crude extracts, purified, or recombinantly expressed, and may be obtained using standard protocols. Proteins may be used as complexes, with and without ligands (e.g. native ligands). In system optimization experiments, in cases where surface binding is not in accord with the expected results from solution binding experiments, the density of oligonucleotides on the surface and the length of the linker between the surface and the oligonucleotide can be varied until specific binding is achieved.

The present invention contemplates the use of a primer extension protocol for creating dsDNA Arrays. Double stranded DNA is the substrate for bioaffinity assays with certain proteins. There are several options for the creation of double stranded DNA arrays, and all of these may be used in the practice of the present invention. One is to hybridize every probe on the surface with its perfect complement. Another option is to design self-complementary palindromes interrupted at the center by a TCCT sequence to facilitate the formation of DNA hairpins displaying the desired dsDNA sequence. The addition of three constant base pairs on either side of the protein binding portion of dsDNA has been shown to buffer the core of the hairpin stem against thermal end-fraying of the duplex and against deviations from B-form DNA. The downside to using hairpin DNA is that long photolithographically synthesized oligonucleotides are required, and the fraction of full length oligonucleotides decreases with increasing length because per base reaction efficiencies are approximately 98%.

The instant invention contemplates creation of dsDNA on the substrate by primer extension. Primer extension involves photolithographic synthesis of a two part oligonucleotide probe. The first part, placed at the beginning of every oligonucleotide, is a primer complement. The second part is the actual probe sequence used in bioaffinity assays. A primer is added to the substrate, allowed to hybridize to its surface-immobilized complement, and then extended with DNA polymerase in the presence of dNTPs. This process has been used with success in another application, DNA computing (Wang et al. 2000, *J. Am. Chem. Soc.* 122: 7435-7440). The specificity experiments described above can be repeated, and the oligonucleotide density and spacer length can be adjusted accordingly to create substrates with good protein binding efficiency and specificity. It is possible to further characterize the surface by eluting the extended primers, phosphorylating them with ATP-$\gamma$-$^{32}$P, and separating them on a PAGE denaturing gel to visualize the distribution of oligonucleotide lengths produced. Using this method, it is possible to obtain a profile of primer extension lengths equivalent to the profile of oligonucleotide lengths displayed on the substrate.

The present invention contemplates the use of Mass Spectrometric (MS) analysis. There are three important pieces of information that can be obtained by mass spectrometry for identifying surface-bound proteins: the molecular weight of the intact proteins; molecular weights of tryptic peptides from those proteins; and sequence information from the tryptic peptides or from the small proteins. The masses of the intact proteins can be determined by direct MALDI analysis of proteins on the substrate or by eluting the proteins from the substrate and analyzing them by either ESI or MALDI. The masses of tryptic peptides can be determined either from MALDI or Direct Ionization on Carbon (DIOC) on the substrate or from surface eluates using ESI or MALDI. Sequence information for tryptic peptides or small proteins can be obtained using tandem-MS methods. The above MS analyses may be employed either individually or in concert according to the demands of each particular experiment.

In one aspect, direct Matrix Assisted Laser Desorption Ionization (MALDI-TOF) on the amorphous carbon substrates may be used to identify the intact proteins that are captured on features of an array. This approach represents the simplest, quickest and most direct method to analyze proteins and is especially useful when the analyte mixture is of known composition. In most cases the denaturing ability of the organic solvent employed in making the MALDI matrix solution is likely to disrupt any specific interactions between proteins and other molecules. However, if they are not desorbed by the organic solvent, it could lead to increased detection limits for direct MALDI on the amorphous carbon substrate. If such a problem presents itself, it could be addressed in a couple of ways. First, a mass-spec "friendly" surfactant (Norris et al., 2003, *Anal. Chem.* 75: 6642-6647) can be applied either prior to or during application of matrix. Second, it is possible to systematically explore other solvents, acids, bases and matrices to enhance release of the protein from the substrate. Third, if protein binding is a combination of specific and non-specific interactions, the non-specific interactions could be disrupted by employing a mixed monolayer within the array feature that is composed both of reactive alkenes for immobilization of the capture agent and of fluorinated alkanes or polyethylene glycols. The incorporation of fluorinated molecules or polyethylene glycols would be expected to reduce non-specific sources of protein binding causing the captured protein to be desorbed more readily.

The present invention contemplates the trypsin digestion of proteins captured on the amorphous carbon:metal substrate. After proteins are captured and SPR imaged, they may be subjected to on-substrate tryptic digestion. Trypsin may be added directly to each spot with or without the use of reduction and alkylation steps. In preliminary experiments and when optimizing conditions, mass-spec friendly detergents and/or organic solvents may be used, and the optimum length of time for the digestion reactions may be determined. The substrate architecture may also be modified to include a hydrophobic border around each spot to "pin" the digestion solution to each specific feature, hence preventing unwanted mixing and contamination from bordering features.

The present invention contemplates peptide and protein elution from the substrate. In preliminary experiments and when optimizing conditions, the parameters explored are the number of wash steps, make-up of the elution buffer (salts, amount of organic solvent), and amount of time left on the chip. Known solutions may be used as the test sample and the sequence coverage and confidence of database matches may be used as the metric to determine the best set of conditions, to ensure that the elution conditions are sufficiently general for the desired application.

Examples

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims.

The following examples are offered to illustrate, but not to limit the claimed invention.

All reagents were purchased from Sigma Aldrich (St. Louis, Mo.) and used without further purification unless otherwise stated.

Silanization of Glass Slides

Figure 4A:
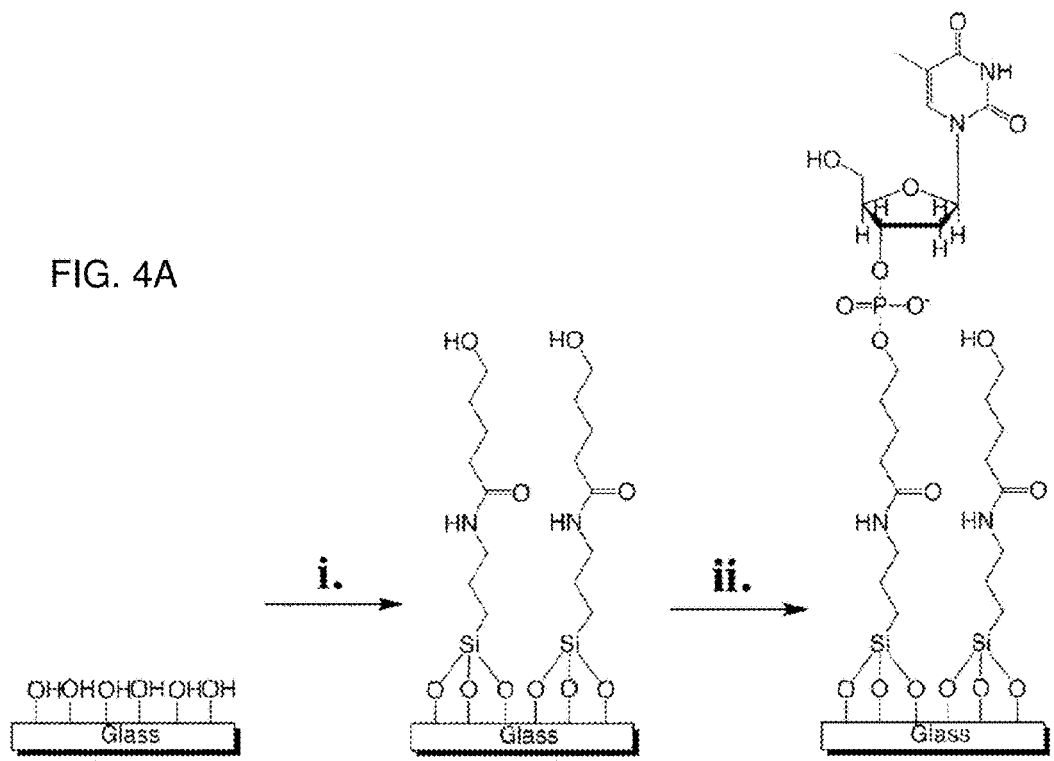
FIGS. 4A and 4B depict an example of surface functionalization according to the present invention.
Figure 4B:
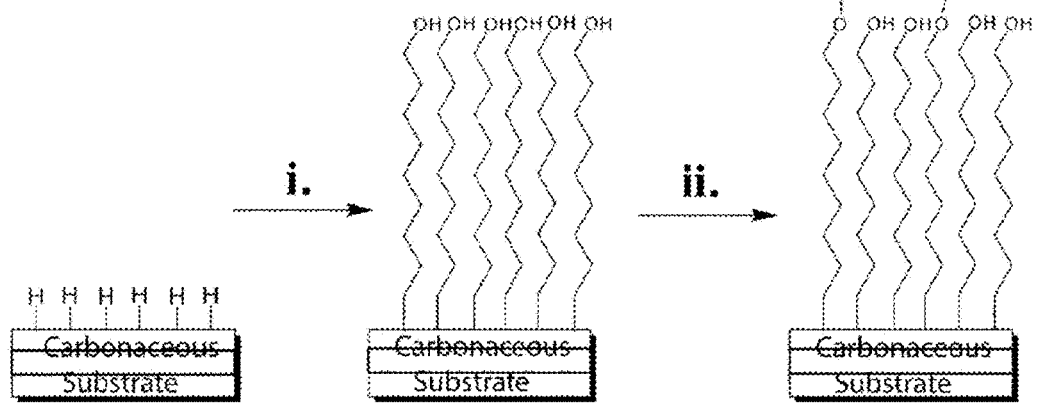

A 0.1% acetic acid in 95% ethanol stock solution was prepared. Arraylt SMC Superclean glass slides (Telechem International, Inc., Sunnyvale, Calif.) were stirred in 2% (v/v) N-(3-triethoxysilylpropyl)-4-hydroxy-butyramide (Gelest, Inc., Morrisville, Pa.) in stock solution for 4 hr at room temperature (RT). The slides were then rinsed by stirring in fresh stock solution for 15 min. After being rinsed 3× in diethyl ether, slides were transferred to a preheated (120° C.) oven for a minimum of 2 hr, after which time they were cured under vacuum overnight. Slides were stored desiccated until used. This is schematically illustrated in FIG. 4a, and is also described in Phillips et al., 2008, *Nucl. Acids Res.* 36: e7.

Preparation of Amorphous Carbon SPR Surfaces

FIG. 3 shows an example of preparation of amorphous carbon SPR surfaces. The amorphous carbon substrates used throughout this work were prepared on (a) high index glass substrates (SF10 glass, Schott Glass, Duryea, Pa.). Prior to use, each glass substrate was rinsed with copious amounts of deionized water (DI) and dried under a stream of nitrogen gas. (b) Metal thin films were applied to the substrate using an Angstrom Engineering Å mod metal evaporator (Cambridge, ON). First, a 2.0 nm chromium thin film was thermally evaporated onto the substrate, providing increased adhesion of the subsequent layers to the SF10 glass. Next, the SPR-active metal of interest was electron-beam evaporated onto the surface: 42.5 nm gold, 40 nm silver, or 42.5 nm copper. (c) Directly after metal evaporation, amorphous carbon thin films were applied to the surface by DC magnetron sputtering (Denton Vacuum, Moorestown, N.J.). The amorphous carbon substrates were chemically functionalized using a modified procedure for the functionalization of diamond substrates, as described in Strother et al., 2002, *Langmuir* 18: 968-971. First, as shown in FIG. 3(d), each amorphous carbon thin film was hydrogen-terminated in a 13.56 MHz inductively coupled hydrogen plasma for 12 minutes (30 Torr $H_2$, room temperature). Next, as shown in FIG. 3(e), 30 μL of 9-decene-1-ol (Sigma Aldrich, St. Louis, Mo.) was placed directly onto the newly hydrogen-terminated surface and covered with a quartz coverslip. The substrates were then irradiated for 8 hours with a low-pressure mercury grid lamp ($\lambda_{max}$=254 nm, 0.35 mW/cm$^2$), under nitrogen purge. After the photoreaction the substrates were rinsed with copious amounts of ethanol and DI, dried under a nitrogen stream, and stored in a desiccator until needed.

Hydrogen Termination of Amorphous Carbon Substrates

Prior to functionalization, the amorphous carbon substrates of the present invention were hydrogen-terminated with a 13.56 MHz inductively coupled H-plasma for 12 min at 30 Torr to generate a hydrogen terminated surface. This is schematically illustrated in FIG. 3d.

Generation of Free Alcohol Groups on Carbon Substrates

Following hydrogen termination, the carbon surfaces were photochemically functionalized by placing 30 μl of 9-decene-1-ol directly onto the surface and covering with a clean quartz coverslip. The surfaces were irradiated under $N_2$ purge with a low-pressure mercury vapor quartz grid lamp ($\lambda$=254 nm) for 8-12 hr. After the photoreaction, the surfaces were briefly rinsed with ethanol and then DI $H_2O$. The surfaces are then stored desiccated until used.

In Situ Oligonucleotide Array Synthesis on Amorphous Carbon Substrates

All of the oligonucleotide arrays used in this work were fabricated using a previously described light-directed photolithographic synthesis method (Singh-Gasson et al., 1999, *Nat. Biotech.* 17: 974-978), allowing the oligonucleotide sequences to be synthesized in a base-by-base manner. Syntheses were performed with oligonucleotide bases modified with a photolabile 3'-nitrophenylpropyloxycarbonyl-(NPPOC—) protecting group and a digital micromirror-based Biological Exposure and Synthesis System (BESS) connected to a Perspective Biosystems Expedite Nucleic Acid Synthesis System (Framingham, Mass.).

Array synthesis proceeded as follows: (a) after condensation of the previous NPPOC-protected base to the growing DNA strand, the synthesis flow cell (volume ~100 μl) was flushed with 500 μl of exposure solvent; (b) a digital image (mask) representing the locations for the next base addition illuminated the surface with 3.95 J/cm$^2$ of 365 nm light (200 W Hg/Xe arc lamp, Newport, Stratford, Conn.). Exposure solvent was constantly flowed through the flow cell at a rate of 100 μl/0.5 J/cm$^2$ during illumination, sufficiently maintaining the basic conditions needed to drive the photocatalyzed elimination reaction. (c) Following irradiation, the array was washed with acetonitrile (~400 μl) to remove residual exposure solvent, dry wash (~300 μl) to remove trace water, and activator solution (~100 μl). (d) Coupling of the next base was achieved by filling the flow cell with a 1:1 solution of the desired phosphoramidite and activator. All 5'-NPPOC-protected amidites underwent a single 40 s coupling step. (e) After amidite coupling, the array was washed with acetonitrile (~100 μl) and either oxidized by flushing the cell with oxidizer solution (THF, pyridine, iodine, and water; ~500 μl) or subjected to the next phosphoramidite addition. The non-acidic conditions of deprotection allow for oxidation of the backbone phosphite groups after every 4th coupling step and at the end of the synthesis, rather than at every coupling step. (f) After synthesis is completed, the nucleoside bases are deprotected in 1:1 ethylenediamine:absolute ethanol solution at room temperature for 2-4 hr.

Oligonucleotide synthesis reagents (DCI activator, acetonitrile (dry wash and amidite diluent), and oxidizer solution) were purchased from Sigma-Proligo, exposure solvent was purchased from Nimblegen Systems Inc. (Madison, Wis.). All anhydrous reagents were kept over molecular sieves (Trap Packs, Aldrich). All NPPOC-protected phosphoramidites [5'-NPPOC-dAdenosine(tac) 3'-β-cyanoethylphosphoramidite (dA), 5'-NPPOC-dThymidine 3'-β-Cyanoethylphosphoramidite (dT), 5'-NPPOC-dCytidine(ib) 3'-β-cyanoethylphosphoramidite (dC), 5'-NPPOC-dGuanosine (ipac) 3'-β-cyanoethylphosphoramidite (dG)] were manufactured by Proligo Biochemie GmbH (Hamburg, Germany) and purchased from Nimblegen Systems Inc.; NPPOC-Phosphoramidites were diluted (1 g in 60 mL) with dry acetonitrile (amidite diluent).

Table 1 contains examples of probe sequences synthesized on low density arrays. The 3' end of sequences 2-4 were separated from the surface by a 10-thymidine spacer, providing a distance of ~30 Å from the surface; this has been shown to increase hybridization efficiency (Guo et al., 1994, Nucleic Acids Research 22: 5456-5465). Probe 1 was terminally labeled with Cy3 while sequences complementary to probes 2-4 in Table 1 were modified at the 3' end with a fluorescein label. For hybridization density determination, sequence 4 (SEQ ID NO:4) was used; all other data presented is only for sequence 1 (SEQ ID NO:1), in order to simplify the analysis.

TABLE 1

Examples of probe sequences synthesized on low density arrays

| Probe sequence | Sequence: 3' → 5' |
|---|---|
| 1 (SEQ ID NO:1) | TTTTTTTTTT-Cy3 |
| 2 (SEQ ID NO:2) | (T)$_{10}$TTATTGAAACGTTGTCACC |
| 3 (SEQ ID NO:3) | (T)$_{10}$GTTATTGAAACGTTGTCACT |
| 4 (SEQ ID NO:4) | (T)$_{10}$GGCTACTGGACGTTCTCA |

DNA Hybridization and Washing

Complementary oligonucleotides for probes 2-4 were purchased from IDT (Coralville, Iowa) and the University of Wisconsin—Madison Biotechnology Center (Madison, Wis.). All arrays were hybridized by placing 30 μL of the fluorescently-tagged complement (1 μM, 1×SSPE [10 mM NaH$_2$PO$_4$, 0.15 M NaCl, 1 mM EDTA, pH=7.4], 45° C.) on the surface, covering with a coverslip, and incubating for 1 hr in a humid chamber. Nonspecifically bound DNA was removed by incubating the surface in 1×SSPE for 15 min at 37° C. Dehybridization was achieved by incubating the surfaces in 8 M urea (RT, 20 min). Unless otherwise noted, fluorescence scans were taken on a Genomic Solutions GeneTac UC 4×4 scanner (Ann Arbor, Mich.). Arrays hybridized with fluorescein-labeled complementary DNA strands were scanned in 1×SSPE.

Determination of Hybridization Density

Hybridization density was determined using a wash-off method as described previously (Peelen et al., 2005 Langmuir 21: 266-271). Arrays consisting of a single sequence (SEQ ID NO:4) were synthesized over the entire (1 cm×1.3 cm) synthesis area. After hybridization and washing, the array was transferred to 20 mL of 8M urea in a 50 mL falcon tube and shaken vigorously for 15-20 min. Calibration solutions containing fluorescein-labeled target DNA (1×10$^{-11}$ to 1×10$^{-8}$ M) were prepared in 8M urea. Using a fluorescence plate reader (BIOTEK, Flx 800, 200 μL per well), the fluorescence from the calibration solutions and unknown samples were measured and the density of hybridized DNA was calculated.

Thermal Stability Determination

In a stirring isothermal water bath, 40 mL of 2×SSPE with 0.2% (v/v) SDS was pre-warmed to either 37° C. or 60° C. in 50 mL falcon tubes fitted with stir vanes. After an initial scan, arrays were incubated at one of the indicated temperatures. At pre-determined time points (0, 0.5, 1 hr-4 hr in 1 hr intervals, and 4 hr-24 hr in 2 hr intervals) the arrays were removed from the solution, rinsed with a room temperature solution of 1×SSPE and hybridized before being scanned and returned to the warm 2×SSPE-SDS solution to continue incubating.

Hybridization Stability Determination

Arrays were subjected to 20 hybridization cycles: hybridized as described above, scanned, incubated in 8 M urea at room temperature for 20 minutes, rinsed with water, 1×SSPE, and another hybridization step was performed. Complete dehybridization was verified by fluorescence imaging.

FTSPR Experimental Conditions

FIG. 5 illustrates the FTSPR instrument configuration and experimental setup. A FTSPR 100 instrument (GWC Technologies, Madison, Wis.) was used to characterize the angle- and wavelength-dependent effects of the amorphous carbon thin films on gold and silver thin film substrates. Shown in FIG. 5(a), a light beam from the external port of a Fourier transform near infrared (FT-NIR) spectrometer is focused onto an aperture and recollimated with a second lens. Shown in FIG. 5(b), the light beam is then polarized with an NIR film polarizer, efficient over the 6000-12000 cm$^{-1}$ range. In a typical experiment, a reference spectrum is acquired with light perpendicular (s-polarized) to the incident plane. Subsequent spectra are acquired with light parallel (p-polarized) to the incident plane. Each spectrum is corrected by ratioing the p- to s-polarized light intensities. Shown in FIG. 5(c), once polarized the light beam is directed onto the substrate, mounted in a Kretschmann configuration. The substrate is attached to a rotating stage, shown in FIG. (d), with an angular precision of 0.001° with a wavelength precision of 0.01 cm$^{-1}$. The light reflected from the substrate is focused onto an InGaAs photodiode detector, as shown in FIG. 5(e).

To achieve the proper configuration for photon-plasmon coupling, a Kretschmann configuration is used. This configuration consists of (f) a prism mounted to the (g) substrate with a layer of index matching fluid (n=1.721, Cargille, Cedar Grove, N.J.). Spectra were recorded after the flow cell was filled with deionized water. The Kretschmann configuration may be optionally mounted to a flow cell, e.g. via a Teflon o-ring, and connected to a peristaltic pump.

SPR Imaging Experimental Conditions

Figure 6D:
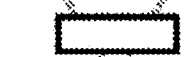
Figure 6E:

FIG. 6 illustrates SPRi instrument configuration, substrate configuration (prism, substrate, flow cell), and experimental conditions. An SPR Imager II instrument (GWC Technologies) was used for all SPRi binding experiments. FIG. 6(a): a collimated white light source is (b) polarized with a visible film polarizer. In a typical experiment a reference image is collected with s-polarized light. Subsequent images are acquired with p-polarized light and corrected by ratioing each image with the reference. FIG. 6(c): the polarized light beam is directed onto the substrate, mounted in a Kretschmann configuration. The configuration is set to a fixed angle throughout the experiment. The optimal angle is substrate dependent and is determined experimentally as approximately 60% of the attainable reflectance. The light reflected from the substrate is refocused and passed through a (d) narrow band pass filter onto a (e) CCD camera.

Surface Plasmon Resonance (SPR) Experiments

FIG. 6 shows an example of typical surface plasmon resonance (SPR) experiments. A typical SPR experiment involves a gold thin film modified with an alkyl thiol self-assembled monolayer, such that molecules of interest can be covalently attached to the surface (e.g. DNA). The binding of solution-phase analytes (e.g. complementary DNA) to the modified surface causes a change in the metal:aqueous interface index of refraction. These changes result in an angular shift of the metal's surface plasmon resonance signature. FIG. 7(a): scanning angle SPR involves coupling the metal film to a prism (Kretschmann configuration) in order to provide the proper orientation for photon-plasmon coupling. The reflectivity of light from the metal thin film is measured as a function of the incident angle, θ. The angle-dependent nature of the photon-plasmon coupling results in the reflectivity curve shown, where the angle of maximal photon-plasmon coupling (minimal % reflectivity) is termed the "surface plasmon angle." After binding such as hybridization with the complementary oligonucleotide, the change in the index of refraction causes a shift in the surface plasmon angle, which can be used to calculate the amount of binding. FIG. 7(b): surface plasmon resonance imaging (SPRi) experiments typically employ a broad, collimated beam of light reflected at a fixed angle from the prism-coupled metal thin film, and images are collected as a function of time. A patterned array of various molecules (e.g. different oligonucleotide sequences) is created on the metal surface. Before binding, an initial image of the array is collected as a reference for the localized reflectivity intensities at this angle ($\theta_F$). After binding occurs to specific features of the surface, localized shifts in the reflectivity curve result in an increased reflectivity (light blue squares in the image). The plot showing two reflectivity curves (before and after binding) demonstrates the increase in reflected light that occurs at the fixed angle ($\theta_F$) upon binding. These curves are merely for illustration here; the actual SPRi data are represented by the difference image between the before-binding and after-binding images. The difference image reveals which array features have undergone index of refraction changes (binding) and which features have not changed.

Figure 8:
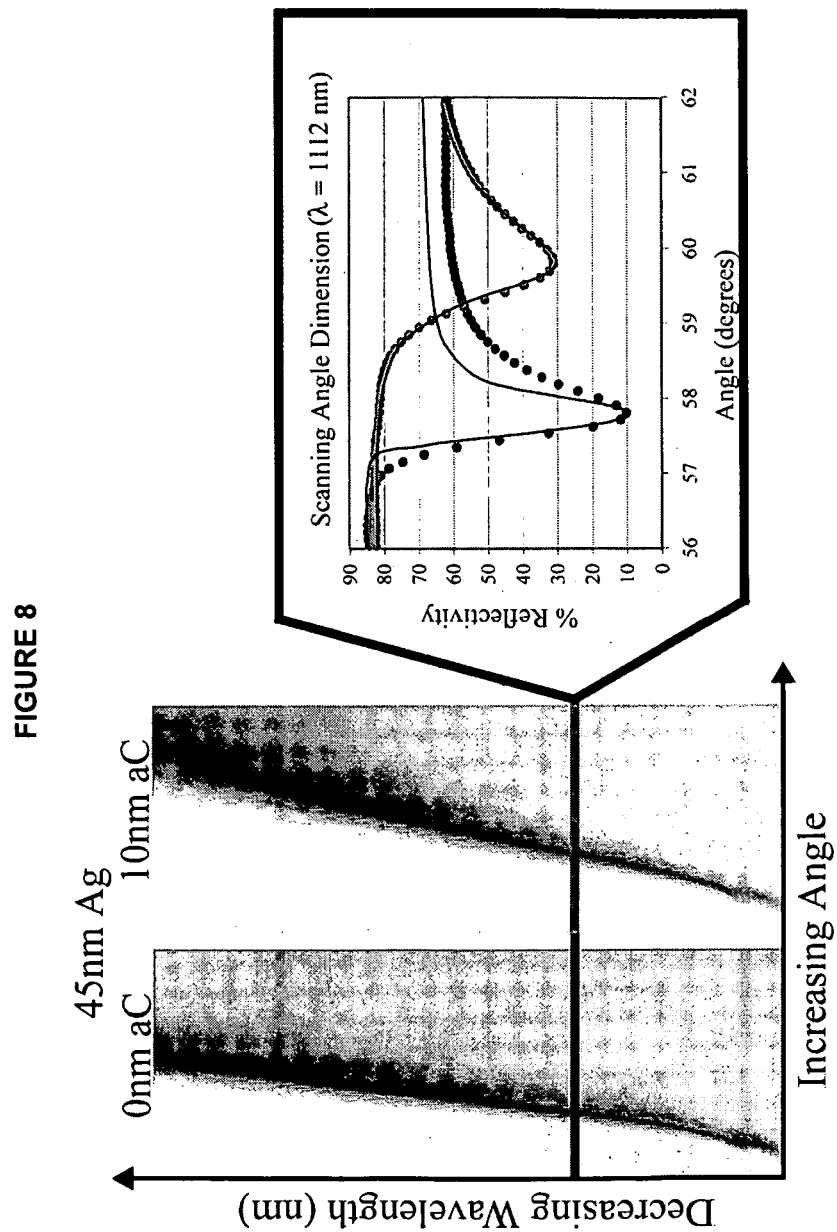
FIG. 8 shows examples of FTSPR measurements with and without an amorphous carbon overlayer.

In some experiments, amorphous carbon overlayers were applied to gold and silver metal thin films and characterized using Fourier Transform Surface Plasmon Resonance (FTSPR) (FIG. 8 and FIG. 9) FTSPR provides a two-dimensional view of a plasmon-supporting material by combining a scanning angle SPR instrument with a Fourier Transform infrared spectrometer. FTSPR scans of the bare metal thin films were compared to analogous substrates coated with a 10 nm amorphous carbon overlayer. FIG. 8 shows examples of SPR measurements with and without an amorphous carbon (aC) overlayer. FTSPR measurements probe the photon-plasmon coupling of a surface in two distinct dimensions: scanning angle (x-coordinate) and scanning wavelength (y-coordinate). FIG. 8(a) shows plots obtained from FTSPR spectra of two (40 nm) silver thin films with a 0 nm (left) and a 10 nm (right) amorphous carbon (aC) overlayer. These three-dimensional images of the surface's photon-plasmon coupling as a function of both angle and wavelength, give qualitative and quantitative information pertaining to optimal conditions for achieving the highest sensitivity. FIG. 8(b) shows scanning angle spectra at a fixed wavelength are shown for both substrates, corresponding to the horizontal line drawn at 1112 nm. Experimental values for the angle-dependent reflectivity of a bare silver film and a silver thin film with a 10 nm amorphous carbon overlayer were compared to theoretically derived values for each substrate (lines). Theoretical values were determined with a n-phase Fresnel calculation.

The broadening of the SPR curves due to the amorphous carbon lead to a loss of surface sensitivity. To evaluate this issue, a series of fixed angle SPR imaging (SPRi) experiments were performed. In these experiments, changes in reflectivity resulting from a $3.0 \times 10^{-4}$ change in the bulk solution index of refraction (caused by replacing pure water, n=1.3333, with a 1% ethanol solution, n=1.3336) were monitored for the bare gold and carbon-gold substrates. The changes in reflectivity for each substrate were compared to that for bare gold substrate and normalized accordingly. FIG. 9 shows data from experiments with varying thicknesses of amorphous carbon that were applied to 42.5 nm gold thin films, which were then characterized with FTSPR measurements, and monitored with fixed angle SPRi. FIG. 9(a): scanning angle reflectivity curves (8994 cm$^{-1}$) of gold substrates containing 5, 7.5, 10, and 12.5 nm of amorphous carbon were compared to a bare gold substrate. Spectra were obtained from FTSPR measurements of the individual substrates. Experimentally obtained values (circles) were compared to theoretically calculated reflectivity curves for each substrate (lines). The theoretical values were determined with an n-phase Fresnel equation. FIG. 8(b): a series of fixed angle SPRi measurements were made to determine the effect of the amorphous carbon overlayer on binding sensitivity. Each substrate was exposed to two solutions with a 0.03% index of refraction difference and the change in reflectivity measured. The total change in reflectivity obtained for the bare gold substrate was used to define a range from 0 to 1 (0=minimum reflectivity; 1=maximum reflectivity); the total change in reflectivity obtained for the carbon-gold substrates is shown as a fraction of that value. A second-order polynomial fit has been added to this graph to guide the eye. For instance, a 7.5 nm amorphous carbon thin film results in a 42% loss of sensitivity relative to a bare gold film (FIG. 9), where sensitivity is defined as the maximum change in reflectivity as a function of refractive index change.

DNA-DNA Binding Experiment

FIG. 10 exemplifies data from DNA-DNA binding experiments. Array design: a 420-oligonucleotide feature array (128 μm×128 μm per feature, with a 96 μm spacing between each feature) was fabricated on a substrate containing 7.5 nm of amorphous carbon sputtered onto a 42.5 nm gold thin film. The array in FIG. 10(a) contained 58 reference features, 17 features of Probe 1, 17 features of Probe 2, and 328 oligonucleotide features that were randomly generated. FIG. 10(b): the reference features within the array are less intense, due to the fact they are 8 nucleotides shorter in length than the other features (18 nucleotides). Each oligonucleotide sequence contained a 10 dT spacer, providing some distance from the surface for increased oligonucleotide hybridization efficiency. Complementary oligonucleotides were synthesized using standard phosphoramidite chemistries (Integrated DNA Technologies, Coralville, Iowa).

TABLE 2

Examples of oligonucleotides used in DNA-DNA binding experiments

| Sequence Name | | Sequence (5' → 3') |
|---|---|---|
| Reference | (SEQ ID NO:1) | TTTTTTTTTT |
| Probe 1 | (SEQ ID NO:5) | CCACTGTTGCAAAGTTAT |
| Probe 2 | (SEQ ID NO:6) | CGCTTCTGTATATTCATC |
| Complement 1 | (SEQ ID NO:7) | ATAACTTTGCAACAGTGG |
| Complement 2 | (SEQ ID NO:8) | GATGAATATACAGAAGCG |

The array was mounted into an SPR Imager II flow cell and placed in the imager. The flow cell was filled with 1×SSPE buffer (10 mM NaH$_2$PO$_4$, 150 mM NaCl, 1 mM EDTA, pH 7.4), the angle was set to 600, a reference image (using s-polarized light) taken, and the experiment started. First, a 100 nm solution of Complement 1 (1×SSPE) was introduced into the flow cell and binding monitored. Image (c) is the difference image obtained 2 minutes after Complement 1 was introduced. Next, a 100 nm solution of Complement 2 (1×SSPE) was introduced and images collected. Difference image (c) was obtained by subtracting image t=120 s from t=0 s. Difference image (d) was obtained by subtracting image t=240 s from t=120 s.

DNA-Protein Binding

FIG. 11 exemplifies data from DNA-protein binding experiments. Array design: A 32-oligonucleotide feature array (256 μm×256 μm per feature, with a 192 μm spacing between each feature) was fabricated on a substrate containing 7.5 nm of amorphous carbon sputtered onto a 42.5 nm gold thin film. The array consisted of two oligonucleotide sequences, a 19 nt oligonucleotide with known thrombin binding (Probe Thr) and a 52 nt self-complementary oligonucleotide with known virulence factor regulator protein binding (Probe VFR). Probe VFR is self-complementary with a 4 nt (TCCT) loop. A hairpin structure was formed by incubating the surface at 65° C. followed by a slow cooling process. Each oligonucleotide sequence contains a 15 dT spacer.

TABLE 3

Examples of oligonucleotides used in DNA-protein binding experiments

| Name | Sequence (5' → 3') |
|---|---|
| Probe Thr (SEQ ID NO:9) | TTGGTTGGTGTGGTTGGTT |
| Probe VFR (SEQ ID NO:10) | AGGACGGGTATCGTACTAGGTGCA<u>TCCT</u>TGCAC CTAGTACGATACCCGTCCT |

The array was mounted into an SPR Imager II flow cell, filled with thrombin binding buffer (20 mM HEPES, 150 mM NaCl, 2 mM CaCl$_2$, pH 7.4), incubated at 60° C. for 10 minutes, and then slowly cooled to room temperature. This process allows the probe VFR hairpins to form. Next, the flow cell was mounted into the SPR imaging instrument, the angle set to 60°, a reference (s-polarized light) image taken, and the experiment started. First, a 10 μg/mL solution of thrombin (Sigma Aldrich, St. Louis, Mo.) in thrombin binding buffer was introduced into the flow cell and binding monitored. The difference image was obtained 10 minutes after the thrombin was introduced. Next, the flow cell was filled with VFR binding buffer (100 mM HEPES buffer, 1 mM DTT, and 1 mM EDTA; at pH 7.0) and a reference image taken. A 10 μg/mL solution of VFR (Aseem Ansari laboratory, University of Wisconsin Department of Biochemistry) in VFR binding buffer was introduced into the flow cell and binding monitored. The difference image was obtained 10 minutes after VFR was introduced.

Comparisons of Different Array Designs

Fluorescence images of identical array designs on two different substrates are shown in FIG. 12. Sequence 1 is terminally labeled with Cy3 and is presented, while sequences 2-4 are hybridized with their respective fluorescein-labeled perfect match complementary sequence. Both substrates exhibit similar Cy3 intensities and comparably low background fluorescence, sequences hybridized on amorphous carbon (b) exhibit a greater fluorescence than those hybridized on glass. This is consistent with the hybridization density results.

Hybridization Density

The hybridization density of a surface is a measure of the number of probe oligomers that are accessible to bind complementary DNA. Wash-off studies in which DNA is first hybridized to and then eluted from the surface for measurement in solution are a preferred method of analysis as substrate-specific and any quenching effects are minimized or eliminated. The hybridization densities determined for the four surfaces tested in this example are shown in Table 4. The density of fluorescently labeled complementary oligonucleotides hybridized to the surface was approximately between $2.5 \times 10^{12}$ (4 pmol/cm$^2$) for arrays prepared on glass substrates as well as on amorphous carbon substrates of the present invention. These are 50% lower than densities reported for oligonucleotides immobilized on gold ($5 \times 10^{12}$ oligonucleotides/cm$^2$, 8 pmole/cm$^2$), and are 14%-26% below the theoretical maximum oligonucleotide density of $1.7 \times 10^{13}$ oligonucleotides/cm$^2$ (17 pmol/cm$^2$) as calculated when the dsDNA helices are assumed to be tightly packed cylinders with diameters of 2 nm each.

TABLE 4

Number of probe molecules accessible to hybridization with their perfect match DNA complement on various surfaces as measured by the number of target oligomers that can be hybridized and collected

| Substrate | Glass | Amorphous Carbon |
|---|---|---|
| Density (×10$^{12}$) molecules/cm$^2$ | 2.69 | 2.51 |
| Percent deviation | ±0.86% | ±1.52% |

Thermal Stability

Figure 13A:
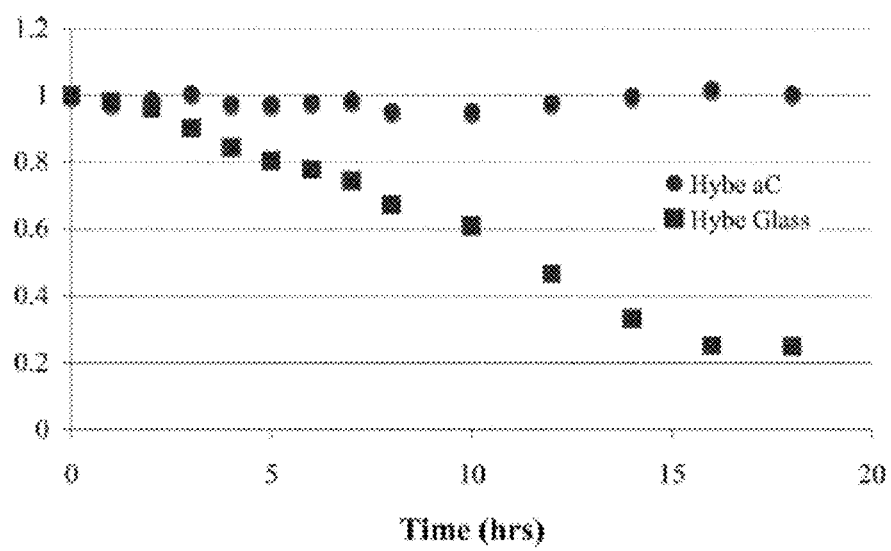
FIGS. 13A and 13B are graphs illustrating the surface stability of arrays prepared on functionalized amorphous carbon substrates and silanized glass compared at 37° (FIG. 13A) and 60° C.
Figure 13B:
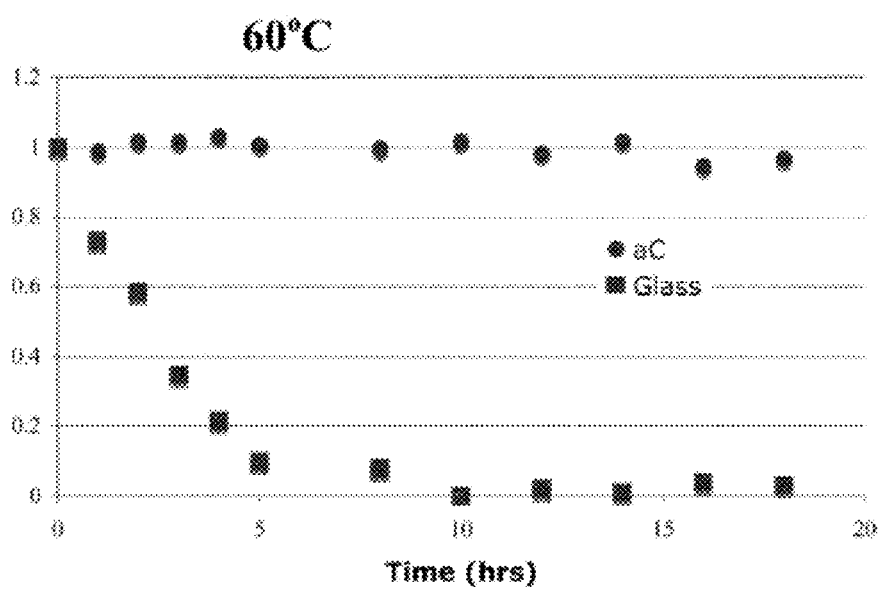

It is often desirable to incubate arrays at higher temperatures. Such temperatures can increase the rate of hydrolysis and lead to problems with array stability. This issue was addressed by comparing, at both 37° C. and 60° C., the surface stability of arrays prepared on the amorphous carbon substrates of the present invention and silanized glass (FIG. 13).

Under both incubation conditions, the amorphous carbon substrates of the present invention exhibited a greater stability than glass. After 18 hrs of incubation at either 60° C. or 37° C., the amorphous carbon substrate of the present invention retained 98±1% of the initial fluorescence signal. Following 20 hrs of incubation at 37° C. glass retained 18±2% of initial fluorescence, and a loss of over 90% was observed after only 6 hrs at 60° C.

Stabilities to Multiple Hybridization Cycles

Figure 14:
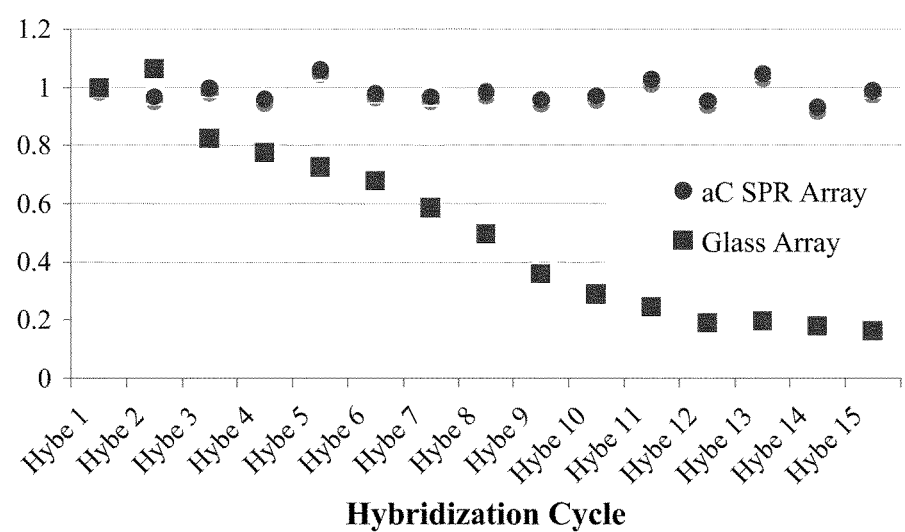
FIG. 14 is a graph illustrating the changes in fluorescence signal for multiple hybridization cycles of arrays prepared on functionalized amorphous carbon substrates and silanized glass.

Incubations in solutions containing either high salt concentrations or helix destabilizing reagents are standard methods to achieve DNA dehybridization. Incubation in 8 M urea for 20 minutes at room temperature is relatively mild yet sufficient to completely dehybridize probe and target molecules. The changes in fluorescence signal for multiple hybridization cycles separated by incubations in 8 M urea solution for 20 min were monitored (FIG. 14). After 20 cycles, glass exhibited 19±2% and the amorphous carbon substrates of the present invention exhibited 98±3% of the initial fluorescence.

Mass Spectrometry

Although SPR imaging is a valuable tool for detecting the binding of biomolecules to surfaces, it does not provide information as to the identity of the binding species. Mass spectrometry offers a powerful complementary tool for the identification of the binding species, and the first implementation of combined SPR and MS was described by Nelson et al., 1997 *Anal. Chem.* 69: 4363-4368. Activity in this area has developed over the intervening years and recent reports describe SPR-MS compatible protein arrays with as many as 100 features (Nedelkov, 2007, *Anal. Chem.* 79: 5987-5990). To date, no MS-SPR substrate has been reported that is as chemically stable and versatile, amenable to photolithographic synthesis, and compatible with direct desorption ionization, as the amorphous carbon:metal substrates described herein.

There are two ionization methods that are employed to produce gas phase ions from biomolecules such as proteins and peptides; matrix-assisted laser desorption/ionization (MALDI), and electrospray ionization (ESI). In MALDI, analyte molecules are dissolved in a solution of small "matrix" molecules and deposited on an electrically conductive substrate. A brief laser pulse, at a wavelength where the matrix absorbs energy, volatilizes the matrix material and carries the analyte molecules with it into the gas phase. Proton transfer reactions from matrix species give rise to analyte protonation (positive ion mode) or deprotonation (negative ion mode), producing gas phase ions. These ions may then be analyzed by time-of-flight (TOF) mass spectrometry to determine their m/z ratios. In ESI, the analyte molecules are dissolved in an aqueous/organic buffer and then directed into a capillary. A large potential is applied between the capillary and the mass spectrometer inlet, which results in the formation of gas phase analyte ions. MALDI gives rise predominantly to singly charged ions, whereas ESI gives rise to a population of multiply charged ions in a wide distribution of charge states.

A simple and direct method of protein identification is by determination of molecular weight. When there is other information available on the nature of the analytes, this is often enough to provide an identification. Alternatively, tandem MS can be employed. In this case the initial ion is fragmented in the gas phase, and the masses of the product ions are determined. The mass differences between the different fragments provide information on the amino acid sequence of the peptide or protein. Another powerful and widely used approach to protein identification is to employ enzymatic digestion of the proteins followed by peptide mass mapping with MALDI-MS or peptide sequencing by ESI-tandem mass spectrometry (ESI-MS/MS). The enzyme trypsin, which cleaves peptides on the C-terminal side of the relatively abundant amino acids arginine (Arg) and lysine (Lys), is the most widely used protease for this application. The confidence of the identification is related to the quality of the mass spectra, and to the number of peptides that are detected in the MS analysis (Thiede et al., 2005, *Methods* 35: 237-247).

Figure 16A:
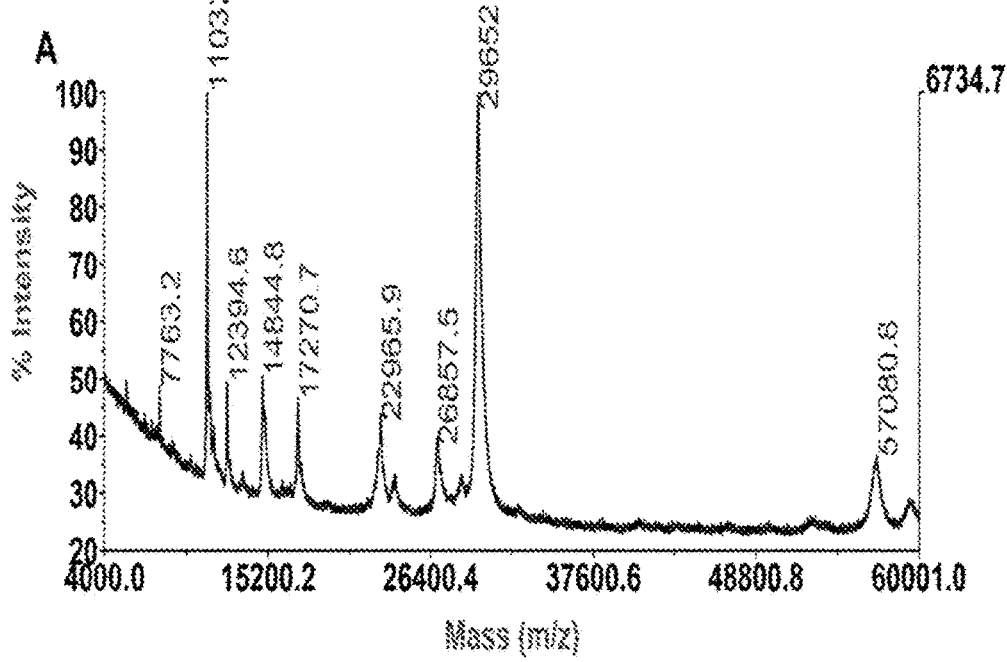
FIGS. 16A and 16B are graphs showing MALDI-TOF mass spectra of a QscR protein sample (5 pmoles) using a standard steel MALDI plate (FIG. 16A) and a carbon-gold substrate (FIG. 16B).
Figure 16B:
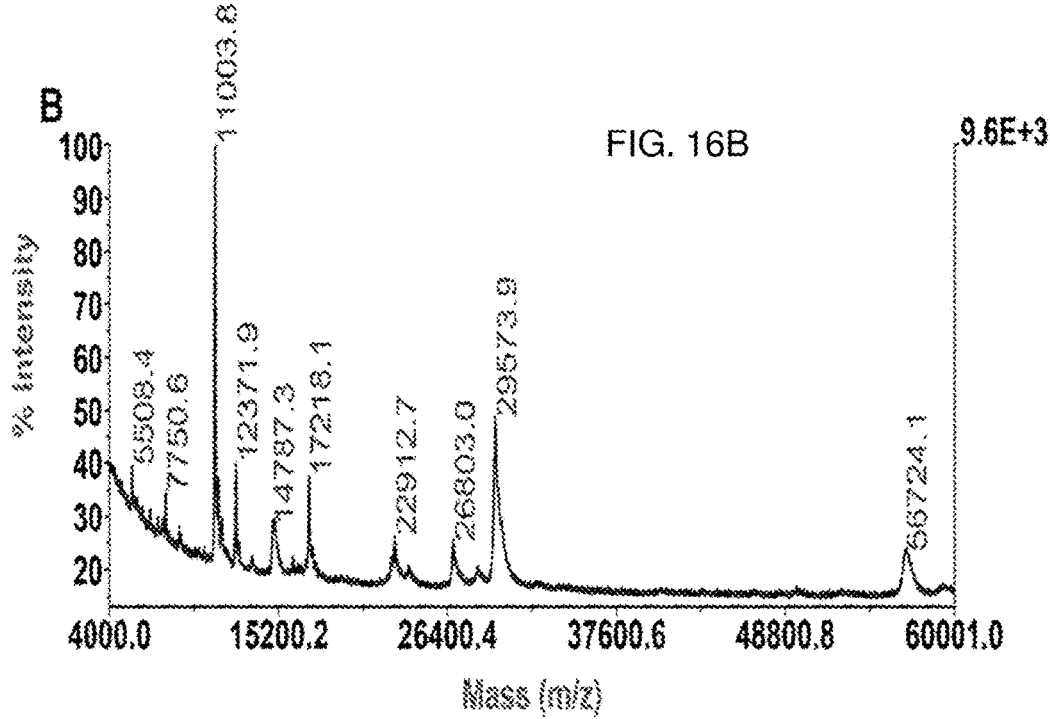

In one aspect this invention brings the power of protein identification methods to work in conjunction with array technology and SPR imaging detection, to identify unknown proteins that are bound to nucleic acid or small molecules on the carbon:metal thin film substrates. FIG. 16 is a graph showing an example of a DIOC-TOF mass spectrum of a 4 mer peptide, GAGR.

On-Substrate Digestion of QscR and HPLC-ESI-MS/MS Analysis

One experiment involved simulates conditions where a protein was captured onto a substrate surface for the purpose of identification. Three different concentrations of intact QscR protein were deposited onto both a standard steel MALDI target and a amorphous carbon:metal substrate (250 fmole, 500 fmole, and 1 pmole). These concentrations correspond roughly with amounts that could be recovered from 1, 2 and 4 mm$^2$ array features. These samples were allowed to dry and were then digested with trypsin at a final protease:protein ratio of 5:1. Digestion was carried out at 37° C. for 5 hours and then the reaction solution was recovered from the surface and transferred into microcentrifuge tubes. The surface was additionally washed with 0.1% TFA/water followed by 0.1% TFA/70% acetonitrile to maximize protein recovery. After desalting, the on-substrate digestion samples were analyzed by HPLC-ESI-MS/MS and then subsequently by MALDI peptide mass fingerprinting. At the 1 pmol level, both QscR and GroEL were confidently identified by tandem MS, although both with lower sequence coverage (for QscR, four peptides matched at high confidence for a sequence coverage of 17.2%). MALDI analyses on both the standard steel MALDI plate and on the carbon substrate produced results similar to one another. At the 250 fmole and 500 fmole levels, only GroEL was identified at high confidence. However, at the 1 pmole level, QscR was confidently identified.

Figure 15A:
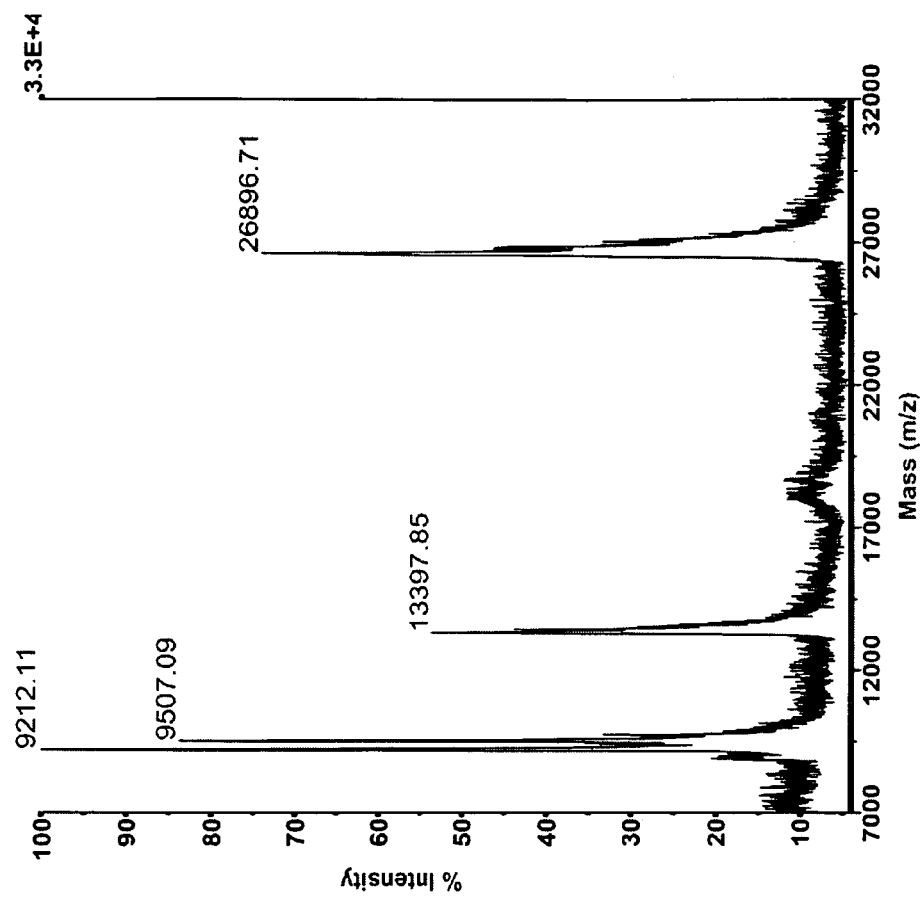
FIG. 15 shows graphs of exemplary mass spectra from proteins and peptides analyzed on different substrates.
Figure 15B:
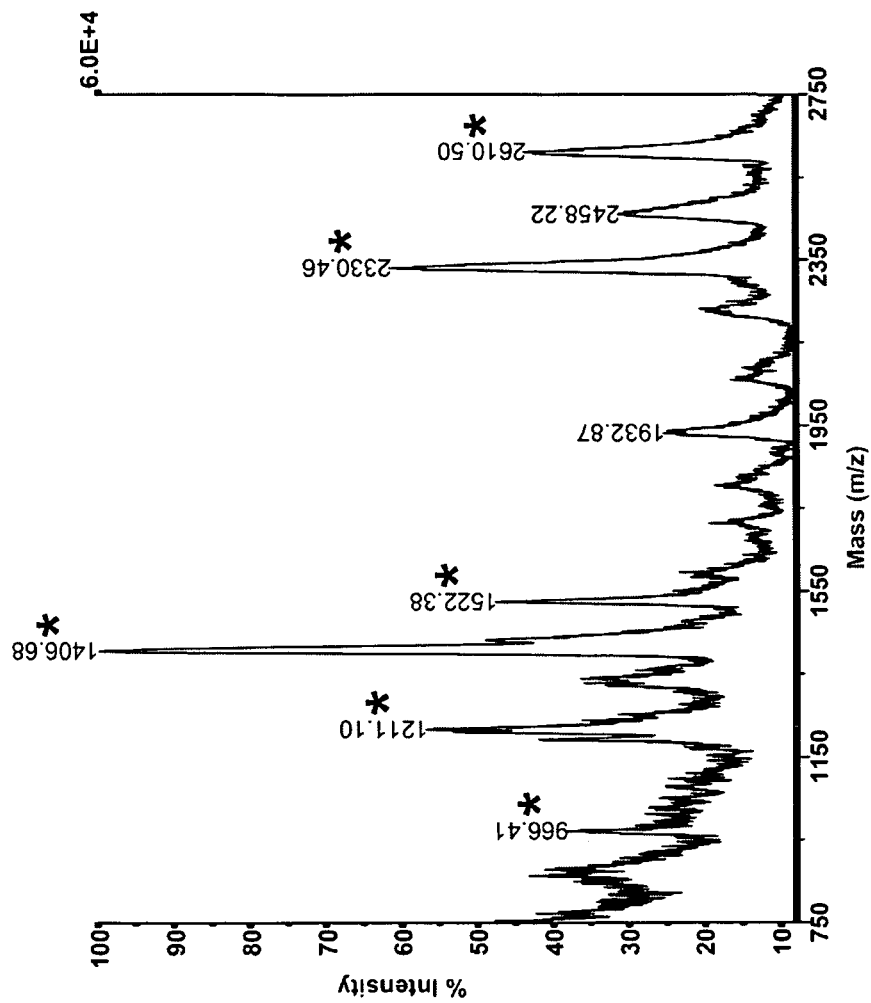
Figure 15C:
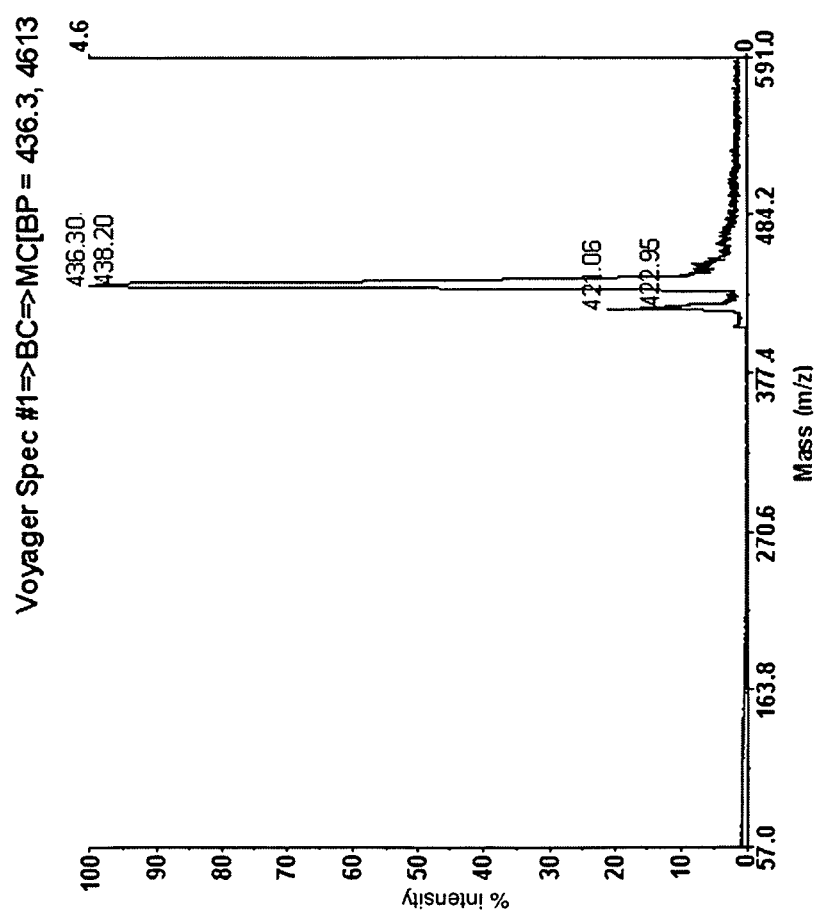

FIG. 15 shows graphs of exemplary mass spectra from proteins and peptides analyzed on different substrates. FIG. 15(A) is a MALDI-TOF of TraR protein (5 pmol) of *A. tumefaciens* analyzed directly on the metal:AC substrate (M+H$^+$ 26.6 kDa and M+2H$^+$ 13.3 kDa). The two other peaks at ~9.5 kDa were identified as HU-alpha and HU-beta by subsequent MS/MS. FIG. 15(B) is a MALDI-TOF of TraR protein digest (5 pmol) on metal:AC substrate. Known tryptic fragments are indicated by the *. FIG. 15(C) is a DIOC-TOF mass spectrum of a 4 mer peptide, GAGR.

FIG. 16 is a graph showing MALDI-TOF mass spectra of a QscR protein sample (5 pmoles) using A) a standard steel MALDI plate and B) a carbon-gold substrate.

Construction of Small Molecule Arrays

The present invention contemplates the construction of small molecule arrays on carbonaceous surfaces for label-free detection of protein interactions with the immobilized species. Small molecule arrays typically require a robust planar support platform. As small molecule arrays are constructed via standard solid-phase synthesis methods, chemical linkers are required for the attachment of the growing molecules and for compound cleavage post-synthesis. Prior to covalent attachment of the linker unit, the entire surface of the planar support is typically derivatized first with a flexible "spacer." This spacer unit is included to improve the accessibility of support-bound molecules for subsequent reactions and for on-support screening.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of chemistry, biochemistry, molecular biology, and bioengineering, are within the scope of this invention. All publications, patents, and patent applications cited herein are incorporated by reference in their entirety for all purposes.

What is claimed is:

1. A substrate, comprising:
   a) a support surface capable of transmitting light;
   b) a metallic layer adhered to the support surface;
   c) a carbonaceous layer deposited on the metallic layer, wherein the carbonaceous layer is configured to substantially protect the metallic layer from exposure to a liquid solution exposed to the carbonaceous layer; and
   d) a plurality of biomolecules covalently attached to the carbonaceous layer.

2. A method for functionalizing a surface to bind biomolecules, the method comprising: a) adhering a metallic layer that can support surface plasmons to a support surface capable of transmitting light; b) depositing carbonaceous material onto the metallic film, to create a carbonaceous layer, wherein the carbonaceous layer is configured to substantially protect the metallic layer from exposure to a liquid solution exposed to the carbonaceous layer; and c) covalently attaching a plurality of biomolecules to the carbonaceous layer, wherein the method yields the substrate as recited in claim 1.

3. The method of claim 2 wherein the support surface is a dielectric material with a high index of refraction.

4. The method of claim 2 wherein the support surface is SF 10 glass.

5. The method of claim 2 wherein the support surface is a SPR-active surface.

6. The method of claim 2 further comprising depositing the carbonaceous material onto the metallic film using DC sputtering.

7. The method of claim 2 wherein the biomolecules are covalently attached to the carbonaceous layer using an ultraviolet light-mediated reaction.

8. The method of claim 2 wherein the biomolecules are configured in one or more arrays.

9. The substrate of claim 1 wherein the carbonaceous layer comprises amorphous carbon.

10. The substrate of claim 1 wherein the carbonaceous layer is selected from the group consisting of amorphous carbon, hydrogenated amorphous carbon, tetrahedral amorphous carbon, and diamond thin film.

11. A substrate, comprising:
   a) a support surface capable of transmitting light in surface plasmon resonance analysis;
   b) a metallic layer capable of undergoing surface plasmon resonance adhered to the support surface;

c) a carbonaceous layer deposited on the metallic layer, wherein the carbonaceous layer is configured to substantially protect the metallic layer from exposure to a liquid solution exposed to the carbonaceous layer and permit the metallic layer to undergo surface plasmon resonance; and d) a plurality of biomolecules covalently attached to the carbonaceous layer.

12. The substrate of claim 11 wherein the support surface comprises a glass block.

13. The substrate of claim 11 wherein the support surface comprises a layer of SF 10 glass.

14. The substrate of claim 11 wherein the carbonaceous layer comprises amorphous carbon.

15. The substrate of claim 11 further comprising a transparent prism adhered to the support surface.

16. The substrate of claim 11 further comprising an index matching fluid positioned between the transparent prism and the support surface.

17. The substrate of claim 11 wherein the biomolecules are attached to the carbonaceous layer at a density of between about $10^{10}/cm^2$ and about $5 \times 10^{14}/cm^2$.

18. The substrate of claim 11 wherein the support surface is selected from the group consisting of plastic, glass, quartz, fused quartz, and fused silica.

19. The substrate of claim 11 wherein the support surface has a thickness of between about 1 µm and about 10 cm.

20. The substrate of claim 11 wherein the metallic layer is selected from the group consisting of gold, silver, copper, chromium, and aluminum.

21. The substrate of claim 11 wherein the metallic layer has a thickness of between about 1 nm and about 1 mm.

22. The substrate of claim 11 wherein the carbonaceous layer is selected from the group consisting of amorphous carbon, hydrogenated amorphous carbon, tetrahedral amorphous carbon, and diamond thin film.

23. The substrate of claim 11 wherein the carbonaceous layer has a thickness of between about 1 nm and about 1 mm.

24. The substrate of claim 11 wherein the biomolecules are configured in one or more arrays.

25. The substrate of claim 11 wherein the biomolecules are selected from the group consisting of single and double-stranded oligonucleotides, DNA, RNA, proteins, protein fragments, amino acids, peptides, aptamers, antibodies, antigens, lectins, carbohydrates, transcription factors, cellular components, cellular surface molecules, viruses, virus fragments, lipids, hormones, vitamins, and small molecules.

26. The substrate of claim 11 wherein the biomolecules are identical to each other.

27. The substrate of claim 11 wherein at least two biomolecules are different from each other.

28. A method of making the substrate as recited in claim 11 for use in surface plasmon resonance measurements, the method comprising: a) adhering the metallic layer that can support surface plasmons to the support surface capable of transmitting light in surface plasmon resonance analysis; b) depositing carbonaceous material onto the metallic layer to create the carbonaceous layer, the carbonaceous layer being configured to substantially protect the metallic layer from exposure to a liquid solution exposed to the carbonaceous layer and permit the metallic layer to undergo surface plasmon resonance; and c) covalently attaching the plurality of biomolecules to the carbonaceous layer.

29. The method of claim 28 further comprising thermally evaporating the metallic layer onto the support surface.

30. The method of claim 28 further comprising depositing the carbonaceous material onto the metallic layer using DC sputtering.

31. The method of claim 28 wherein the biomolecules are covalently attached to the carbonaceous layer using an ultraviolet light-mediated reaction.

32. The method of claim 28 wherein the biomolecules are configured in one or more arrays.

33. A method for detecting surface plasmon resonance associated with a test sample, the method comprising: a) providing a substrate comprising a support surface capable of transmitting light in surface plasmon resonance analysis; a metallic layer capable of undergoing surface plasmon resonance adhered to the support surface; a carbonaceous layer deposited on the metallic layer, wherein the carbonaceous layer is configured to substantially protect the metallic layer from exposure to a liquid solution exposed to the carbonaceous layer and permit the metallic layer to undergo surface plasmon resonance; a plurality of biomolecules covalently attached to the carbonaceous layer; b) contacting the test sample with the plurality of biomolecules attached to the carbonaceous layer; and c) detecting surface plasmon resonance associated with the test sample.

34. The method of claim 33 wherein the biomolecules are configured in one or more arrays.

35. The method of claim 33 further comprising the step of (d) using mass spectrometric means to analyze molecules from the test sample that are attached to the plurality of biomolecules.

36. An assay comprising: a) providing a substrate comprising a support surface capable of transmitting light; a metallic layer adhered to the support surface; a carbonaceous layer deposited on the metallic layer, wherein the carbonaceous layer is configured to substantially protect the metallic layer from exposure to a liquid solution exposed to the carbonaceous layer; a plurality of biomolecules covalently attached to the carbonaceous layer; b) contacting the test sample with the plurality of biomolecules attached to the carbonaceous layer; and c) analyzing molecules from the test sample attached to the plurality of biomolecules using mass spectrometric means.

37. A substrate suitable for surface plasmon resonance reflectivity measurements, comprising: a) a support surface capable of transmitting light comprising an SF-10 glass block, b) a metallic layer adhered to the support surface comprising an SPR-active metallic film having a thickness in the range of about 1 nm to about 1 µm; c) a carbonaceous layer deposited on the metallic layer comprising a carbon film having a thickness in the range of about 1 nm to about 1 µm, wherein the carbonaceous layer is configured to substantially protect the metallic layer from exposure to a liquid solution exposed to the carbonaceous layer; and d) a plurality of biomolecules covalently attached to the carbonaceous layer.

38. The substrate of claim 37 wherein the SF-10 glass block has a thickness of between about 1 µm and about 10 cm.

39. The substrate of claim 37 further comprising a glass prism adhered to the SF-10 glass block.

40. The substrate of claim 39 further comprising index matching fluid positioned between the SF-10 glass block and the glass prism.

41. The substrate of claim 37 wherein the carbon film comprises amorphous carbon.

42. The substrate of claim 37 wherein the SPR-active metallic film comprises gold.

43. The substrate of claim 37 wherein the biomolecules attached to the carbon film are configured in one or more arrays.

44. The substrate of claim 37 wherein the biomolecules are attached to the carbon film at a density of between about $10^{10}/cm^2$ and about $5\times10^{14}/cm^2$.

* * * * *

```
                             SEQUENCE LISTING

<160> NUMBER OF SEQ ID NOS: 10

<210> SEQ ID NO 1
<211> LENGTH: 10
<212> TYPE: DNA
<213> ORGANISM: Artificial Sequence
<220> FEATURE:
<223> OTHER INFORMATION: Probe 1

<400> SEQUENCE: 1
tttttttttt                                                                 10

<210> SEQ ID NO 2
<211> LENGTH: 29
<212> TYPE: DNA
<213> ORGANISM: Artificial Sequence
<220> FEATURE:
<223> OTHER INFORMATION: Probe 2

<400> SEQUENCE: 2
tttttttttt ttattgaaac gttgtcacc                                            29

<210> SEQ ID NO 3
<211> LENGTH: 30
<212> TYPE: DNA
<213> ORGANISM: Artificial Sequence
<220> FEATURE:
<223> OTHER INFORMATION: Probe 3

<400> SEQUENCE: 3
tttttttttt gttattgaaa cgttgtcact                                           30

<210> SEQ ID NO 4
<211> LENGTH: 28
<212> TYPE: DNA
<213> ORGANISM: Artificial Sequence
<220> FEATURE:
<223> OTHER INFORMATION: Probe 4

<400> SEQUENCE: 4
tttttttttt ggctactgga cgttctca                                             28

<210> SEQ ID NO 5
<211> LENGTH: 18
<212> TYPE: DNA
<213> ORGANISM: Artificial Sequence
<220> FEATURE:
<223> OTHER INFORMATION: Probe 1 DNA-DNA binding

<400> SEQUENCE: 5
ccactgttgc aaagttat                                                        18

<210> SEQ ID NO 6
<211> LENGTH: 18
<212> TYPE: DNA
<213> ORGANISM: Artificial Sequence
<220> FEATURE:
<223> OTHER INFORMATION: Probe 2 DNA-DNA binding

<400> SEQUENCE: 6
```

```
cgcttctgta tattcatc                                                 18

<210> SEQ ID NO 7
<211> LENGTH: 18
<212> TYPE: DNA
<213> ORGANISM: Artificial Sequence
<220> FEATURE:
<223> OTHER INFORMATION: Complement 1 DNA-DNA binding

<400> SEQUENCE: 7
ataactttgc aacagtgg                                                 18

<210> SEQ ID NO 8
<211> LENGTH: 18
<212> TYPE: DNA
<213> ORGANISM: Artificial Sequence
<220> FEATURE:
<223> OTHER INFORMATION: Complement 2 DNA-DNA binding

<400> SEQUENCE: 8
gatgaatata cagaagcg                                                 18

<210> SEQ ID NO 9
<211> LENGTH: 19
<212> TYPE: DNA
<213> ORGANISM: Artificial Sequence
<220> FEATURE:
<223> OTHER INFORMATION: Probe Thr

<400> SEQUENCE: 9
ttggttggtg tggttggtt                                                19

<210> SEQ ID NO 10
<211> LENGTH: 52
<212> TYPE: DNA
<213> ORGANISM: Artificial Sequence
<220> FEATURE:
<223> OTHER INFORMATION: Probe VFR

<400> SEQUENCE: 10
aggacgggta tcgtactagg tgcatccttg cacctagtac gatacccgtc ct           52
```